United States Patent
Erickson et al.

(10) Patent No.: US 10,966,447 B2
(45) Date of Patent: Apr. 6, 2021

(54) GLUCOSYRINGIC ACID ANALOGS AS SWEETNESS PROFILE MODIFIERS

(71) Applicant: PepsiCo, Inc., Purchase, NY (US)

(72) Inventors: Shawn Erickson, Leonia, NJ (US); Yu-Wen Feng, White Plains, NY (US); Christophe Galopin, Rye Brook, NY (US); Stephen Gravina, Rutherford, NJ (US); Yuliya Kurash, Sleepy Hollow, NY (US); Thomas Lee, Scarsdale, NY (US); Laura Nattress, Tarrytown, NY (US); Ting Wang, Delmar, NY (US)

(73) Assignee: PepsiCo, Inc., Purchase, NY (US)

( * ) Notice: Subject to any disclaimer, the term of this patent is extended or adjusted under 35 U.S.C. 154(b) by 661 days.

(21) Appl. No.: 15/213,859

(22) Filed: Jul. 19, 2016

(65) Prior Publication Data
US 2018/0020708 A1 Jan. 25, 2018

(51) Int. Cl.
| A23L 27/30 | (2016.01) |
| A23L 27/00 | (2016.01) |
| A23L 2/56 | (2006.01) |
| A23L 29/30 | (2016.01) |
| A23L 2/60 | (2006.01) |
| A23L 2/68 | (2006.01) |
| C07H 15/203 | (2006.01) |

(52) U.S. Cl.
CPC ............... *A23L 27/33* (2016.08); *A23L 2/56* (2013.01); *A23L 2/60* (2013.01); *A23L 2/68* (2013.01); *A23L 27/30* (2016.08); *A23L 27/84* (2016.08); *A23L 27/86* (2016.08); *A23L 27/88* (2016.08); *A23L 29/35* (2016.08); *C07H 15/203* (2013.01); *A23V 2002/00* (2013.01)

(58) Field of Classification Search
CPC .......... A23L 27/33; A23L 27/88; A23L 27/86; A23L 27/30; A23L 27/84; A23L 29/35; A23L 2/56; A23L 2/60; A23L 2/68; C07H 15/203; A23V 2002/00
USPC .......................... 426/534, 536, 538, 548, 658
See application file for complete search history.

(56) References Cited

U.S. PATENT DOCUMENTS

| 4,830,862 A | 5/1989 | Braun et al. |
| 4,871,570 A | 10/1989 | Barnett et al. |
| 4,925,686 A | 5/1990 | Kastin |
| 7,052,725 B2 | 5/2006 | Chang et al. |
| 8,877,922 B2 | 11/2014 | Tachdjian et al. |
| 2008/0220140 A1 | 9/2008 | Ley et al. |
| 2014/0093630 A1 | 4/2014 | Shigemura et al. |
| 2014/0094453 A1 | 4/2014 | Tachdjian et al. |
| 2014/0271996 A1 | 9/2014 | Prakash et al. |
| 2014/0272068 A1 | 9/2014 | Prakash et al. |

FOREIGN PATENT DOCUMENTS

| JP | 2019024331 A1 | 2/2019 |
| WO | WO2006/087370 A1 | 8/2006 |
| WO | WO2015/009558 A1 | 1/2015 |
| WO | WO 2016/040577 A1 | 3/2016 |

OTHER PUBLICATIONS

National Center for Biotechnology Information. PubChem Compound Database; CID=10383888, https://pubchem.ncbi.nlm.nih.gov/compound/10383888 (accessed Jan. 22, 2019).*
International Search Report for International Application No. PCT/US2017/042605 dated Nov. 13, 2017, 4 pages.
PUBCHEM, Compound Database, SID 274283580, Available Date: Dec. 18, 2015 [retrieved Oct. 26, 2017]. Retrieved from the Internet:<URL:https://oybchem.ncbi.nim.nih.gov/substance/274283580/version/1#section=Top>entiredocument; 6 pages. (2015).

(Continued)

*Primary Examiner* — Leslie A Wong
(74) *Attorney, Agent, or Firm* — Sterne, Kessler, Goldstein & Fox P.L.L.C.

(57) ABSTRACT

The present disclosure provides novel sweetener compositions comprising a compound having a structure according to Formula I:

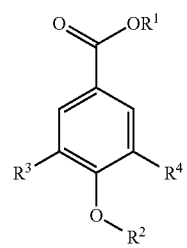

Figure 1:
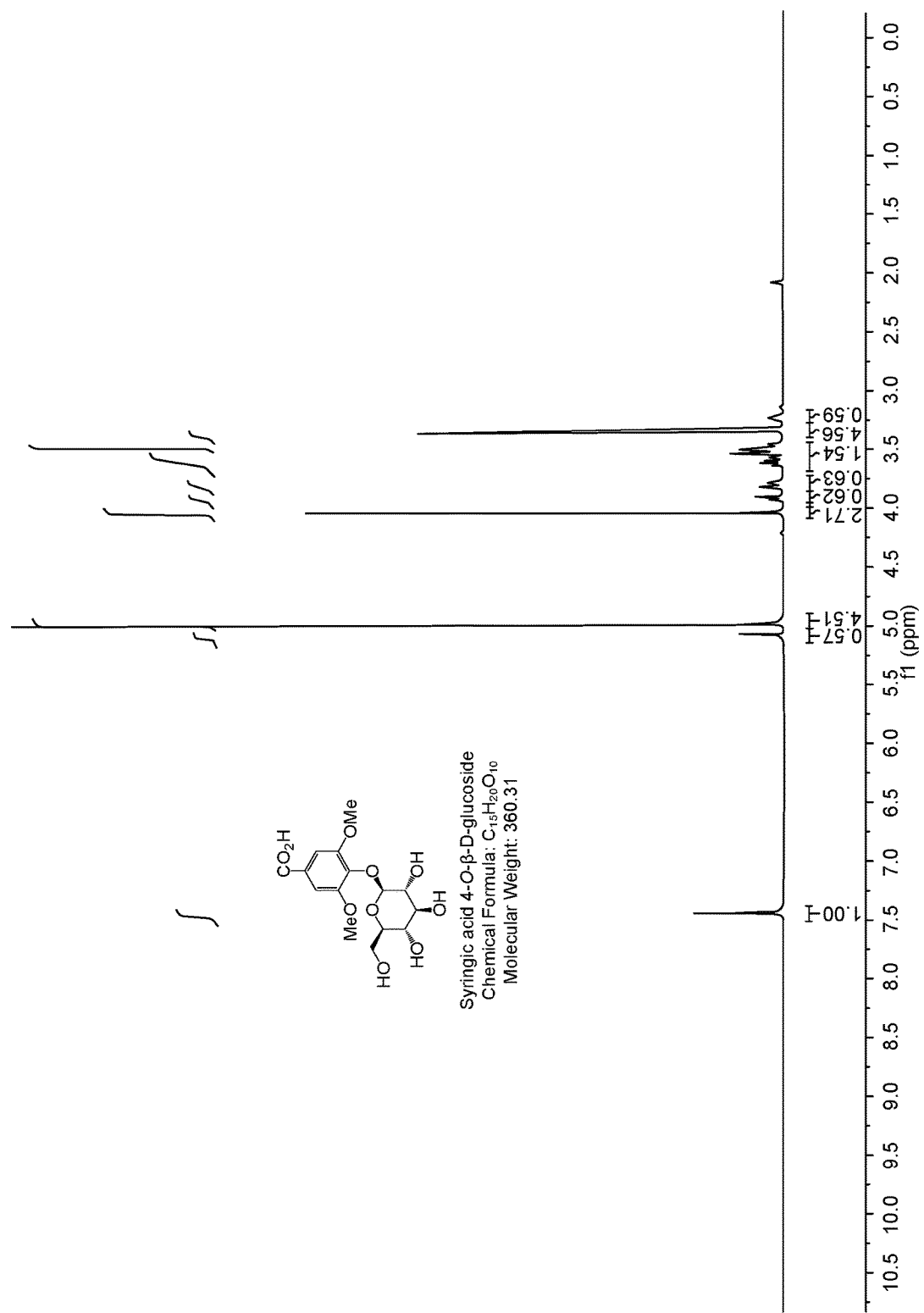

Formula I wherein $R^1$, $R^2$, $R^3$, and $R^4$ are described herein. Also provided are methods of modulating sweetness profile of a product by adding a compound of Formula I to the product, such as a beverage product or a food product. For example, the compound described herein can be added to increase the overall sweetness of a nutritive sweetener sweetened beverages; decrease the sweetness time-of-onset for high potency sweeteners such as rebaudioside A; decreasing bitter, metallic and licorice off-notes of high potency sweeteners; and improve the sweet quality of sweetened products.

14 Claims, 7 Drawing Sheets

(56) References Cited

OTHER PUBLICATIONS

PUBCHEM, Compound Database, SID 274920169, Available Date: Dec. 19, 2015 [retrieved Aug. 22, 2017]. Retrieved from the Internet: <URL:https://pubchem.ncbi.nlm.nih.gov/substance/274920169/version/1 > entire document (2015).
Yu, Hui et al., "Antioxidant activities of aqueous extract from *Stevia rebaudiana* stem waste to inhibit fish oil oxidation and identification of its phenolic compounds," Food Chemistry, 232:379-386, 2017.
Pubchem, Compound Database, SID 90845766, Available Date: Mar. 16, 2015 [retrieved Oct. 27, 2020]. Retrieved from the Internet: https://pubchem.ncbi.nlm.nih.gov/compound/90845766; entire document; 10 pages (2015).

* cited by examiner

GLUCOSYRINGIC ACID ANALOGS AS SWEETNESS PROFILE MODIFIERS

BACKGROUND AND FIELD OF THE INVENTION

The present disclosure is generally directed to compounds useful for modulating sweetness profile of a sweetener.

The food and beverage industry has become interested in high potency sweeteners such as steviol glycosides in the pursuit of alternative sweeteners. However, replacing nutritive sweeteners with known potent non-nutritive sweeteners is difficult due to off-tastes associated with these sweeteners, for example slow on-set, bitter, licorice, or lingering aftertastes. Thus, there remains a need to develop sweetener compositions that better mimic the taste profile as sugar.

BRIEF SUMMARY

In various embodiments, the present disclosure provides a sweetener composition comprising a sweetener and a compound having a structure according to Formula I:

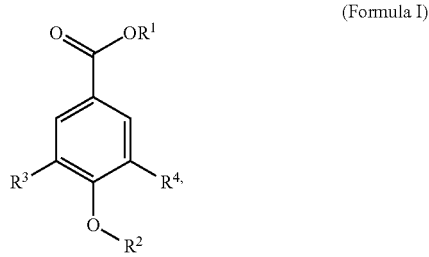

(Formula I)

wherein
$R^1$ is H, Me, or Et,
$R^2$ is a pyranoside selected from the group consisting of glucopyranoside, glucuronopyranoside, rhamnopyranoside, galactopyranoside, deoxyglucopyranoside, and mannopyranoside; and
$R^3$ and $R^4$ are each independently H or MeO,
or a salt thereof.

Typically, the compound of Formula I is present in the sweetener composition in an amount sufficient to decrease one or more of slow-onset, bitterness, licorice, or lingering after tastes. Useful amounts include those ranging from about 30 ppm to about 300 ppm.

Various sweeteners can be included in the sweetener compositions described herein. For example, in some embodiments, the sweetener is selected from the group consisting of a steviol glycoside, Stevia rebaudiana extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and mixtures of any of them. In particular embodiments, the sweetener is high fructose corn syrup or a steviol glycoside such as rebaudioside A.

The sweetener compositions described herein can further include a sweetness enhancer. For example, in some embodiments, the sweetener composition comprises a sweetener enhancer selected from the group consisting of D-psicose, erythritol, rubusoside, rebaudioside B, rebaudioside C, trilobatin, phyllodulcin, brazzein, mogrosides, and combinations thereof.

The sweetener compositions described herein can be in various forms. For example, in some embodiments, the sweetener composition is a dry blend such as a tabletop sweetener composition. In some embodiments, the sweetener composition is an aqueous sweetener composition. In some embodiments, the sweetener compositions can be provided in various products such as beverage products and food products.

In some embodiments, the sweetener compositions described herein can be provided in a beverage product such as a ready-to-drink beverage or a beverage concentrate. For example, in some embodiments, the ready-to-drink beverage comprises water, a sweetener composition comprising a sweetener and a compound of Formula I as described herein, and optionally an acidulant selected from the group consisting of phosphoric acid, citric acid, malic acid, tartaric acid, lactic acid, formic acid, ascorbic acid, fumaric acid, gluconic acid, succinic acid, maleic acid, adipic acid, and mixtures thereof. In some embodiments, the water is carbonated water. In some embodiments, the acidulant is phosphoric acid. In some embodiments, the ready-to-drink beverage comprises a cola flavorant. In some embodiments, the ready-to-drink beverage comprises a tea flavorant. In some embodiments, the ready-to-drink beverage comprises a coffee flavorant. In some embodiments, the ready-to-drink beverage is a low calorie or zero-calorie beverage. In some embodiments, the ready-to-drink beverage further comprises caffeine. In some embodiments, the ready-to-drink beverage is substantially caffeine free. Other suitable ingredients are described herein. In some embodiments, the ready-to-drink beverage is selected from the group consisting of carbonated beverages, non-carbonated beverages, fountain beverages, frozen carbonated beverages, fruit juices, fruit juice-flavored drinks, fruit-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and mixtures of any of them.

In some embodiments, the sweetener compositions described herein can be provided in a food product. For example, in some embodiments, the food product comprises a food component and a sweetener composition comprising a sweetener and a compound of Formula I as described herein. Other suitable ingredients are described herein. In some embodiments, the food product is selected from the group consisting of oatmeal, cereal, baked goods, cookies, crackers, cakes, brownies, breads, snack foods, potato chips, tortilla chips, popcorn, snack bars, rice cakes, and grain-based food products.

In some embodiments, the present disclosure also provides a method of modulating the sweetness profile of a sweetener in a product. In some embodiments, the method comprises adding to the product a compound having a structure according to Formula I. Suitable compounds of Formula I and sweeteners are described herein.

The present disclosure also provides a modulating sweetness profile of a sweetener in a product, comprising adding to the product a compound having a structure according to Formula I.

BRIEF DESCRIPTION OF THE DRAWINGS/FIGURES

The foregoing summary, as well as the following detailed description of the embodiments, will be better understood when read in conjunction with the appended figures. For the purpose of illustration, the figures may describe the use of specific embodiments. It should be understood, however, that the compounds, formulations, compositions, and methods described herein are not limited to the precise embodiments discussed or described in the figures.

FIGS. 1-7 show the $^1$H NMR spectra of the exemplified compounds 5, 6, 8, 9, 15, 19, and 28, respectively.

DETAILED DESCRIPTION

Definitions

Various examples and embodiments of the inventive subject matter disclosed here are possible and will be apparent to the person of ordinary skill in the art, given the benefit of this disclosure. In this disclosure reference to "some embodiments," "certain embodiments," "certain exemplary embodiments" and similar phrases each means that those embodiments are non-limiting examples of the inventive subject matter, and there are alternative embodiments which are not excluded.

Unless otherwise indicated or unless otherwise clear from the context in which it is described, alternative and optional elements or features in any of the disclosed embodiments and examples are interchangeable with each other. That is, an element described in one embodiment or example should be understood to be interchangeable or substitutable for one or more corresponding but different elements in another described example or embodiment and, likewise, an optional feature of one embodiment or example may optionally also be used in other embodiments and examples. More generally, the elements and features of any disclosed example or embodiment should be understood to be disclosed generally for use with other aspects and other examples and embodiments. A reference to a component or ingredient being operative or configured to perform one or more specified functions, tasks and/or operations or the like, is intended to mean that it can perform such function(s), task(s), and/or operation(s) in at least certain embodiments, and may well be able to perform also one or more other functions, tasks, and/or operations.

The articles "a," "an," and "the" are used herein to refer to one or to more than one (i.e., to at least one) of the grammatical object of the article. By way of example, "an element" means one element or more than one element.

The word "comprising" is used in a manner consistent with its open-ended meaning, that is, to mean that a given product or process can optionally also have additional features or elements beyond those expressly described. It is understood that wherever embodiments are described with the language "comprising," otherwise analogous embodiments described in terms of "consisting of" and/or "consisting essentially of" are also provided.

As used herein, the term "about" means±10% of the noted value. By way of example only, a composition comprising "about 30 weight percent" of a compound could include from 27 weight percent of the compound up to and including 33 weight percent of the compound.

The terms "beverage concentrate," "concentrate," and "syrup" are used interchangeably throughout this disclosure and refer to an aqueous sweetener composition suitable for use in beverage preparation. Exemplary embodiments are described elsewhere in this disclosure.

As used herein, the term "Brix" means the sugar content of an aqueous solution (w/w). By way of example only, a solution that is 1 degree Brix contains 1 g of sucrose in 100 grams of solution, while a solution that is 5 degrees Brix contains 5 g sucrose in 100 g solution.

As used herein, the phrase "edible consumables" means a food, beverage, or an ingredient of a food or beverage suitable for human or animal consumption.

The term "sweetness recognition threshold concentration," as generally used herein, is the lowest known concentration of a given sweetener or combination of sweeteners that is perceivable by the human sense of taste, typically around about 1.5% sucrose equivalence.

As used herein, "taste" refers to a combination of sweetness perception, temporal effects of sweetness perception, i.e., on-set and duration, off-tastes, e.g. bitterness and metallic taste, residual perception (aftertaste), and tactile perception, e.g. body and thickness.

The term "nutritive sweetener" refers generally to sweeteners which provide significant caloric content in typical usage amounts, e.g., more than about 5 calories per 8 oz. serving of a beverage.

As used herein, the term "non-nutritive sweetener" refers to all sweeteners other than nutritive sweeteners.

As used herein, a "full-calorie" beverage formulation is one fully sweetened with a nutritive sweetener.

As used herein, a "low-calorie beverage" has fewer than 40 calories per 8 oz. serving of beverage.

As used herein, "zero-calorie" means having less than 5 calories per serving per 8 oz. for beverages.

As used herein, a "potent sweetener" means a sweetener which is at least twice as sweet as sugar, i.e., a sweetener which on a weight basis requires no more than half the weight of sugar to achieve an equivalent sweetness. For example, a potent sweetener may require less than one-half the weight of sugar to achieve an equivalent sweetness in a beverage sweetened to a level of 10 degrees Brix with sugar. Potent sweeteners include both nutritive (e.g., Lo Han Guo juice concentrate) and non-nutritive sweeteners (e.g., typically, Lo Han Guo powder). In addition, potent sweeteners include both natural potent sweeteners (e.g., steviol glycosides, Lo Han Guo, etc.) and artificial potent sweeteners (e.g., neotame, etc.).

As used in this disclosure, unless otherwise specified, the term "added," "combined," and terms of similar character mean that the multiple ingredients or components referred to (e.g., one or more sweeteners, sweetness enhancers, etc.) are combined in any manner and in any order, with or without stirring.

Sweetener Compositions Comprising GSA Analogs

In various embodiments, the present disclosure provides a sweetener composition comprising a compound that can modify the sweetness profile of a sweetener, for example, to increase the overall sweetness, decrease the sweetness time-of-onset, decrease bitter, metallic and licorice off-notes, and/or improve sweet quality (e.g., roundness) of the sweetener. In some embodiments, the compound is glucosyringic acid (GSA) or an analog thereof.

In some embodiments, the compound has a structure according to Formula I:

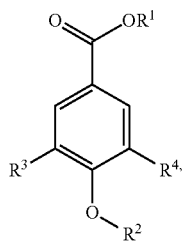
(Formula I)

wherein

R¹ is H, Me, or Et,

R² is a residue of a pyranoside selected from the group consisting of glucopyranoside, glucuronopyranoside, rhamnopyranoside, galactopyranoside, deoxyglucopyranoside, and mannopyranoside; and R³ and R⁴ are each independently a H or MeO.

In some embodiments, the compound of Formula I is in the form of a salt, e.g., an alkali salt such as sodium salt.

In some embodiments, R¹ is H. In some embodiments, R¹ is Me. In some embodiments, R¹ is Et.

Typically, R² is a residue of a beta-pyranoside. However, in some embodiments, R² can also be a residue of an alpha-pyranoside.

Typically, R² is a residue of a D-pyranoside, i.e., the pyranose is in D-configuration. However, in some embodiments, R² can also be a residue of an L-pyranoside, i.e., the pyranose is in L-configuration.

For example, in some embodiments, R² can be a residue of a beta-D-glucopyranoside or beta-D-glucuronopyranoside. In some embodiments, R² can have a structure of:

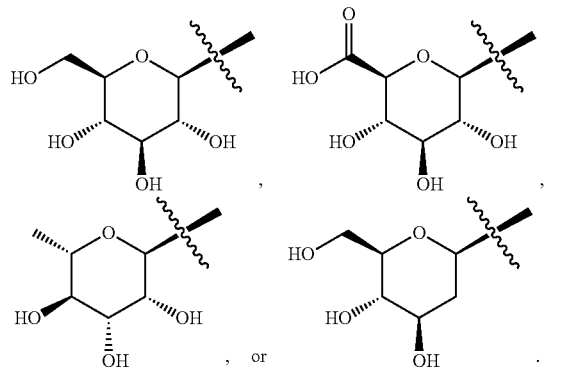

In some particular embodiments, R² is

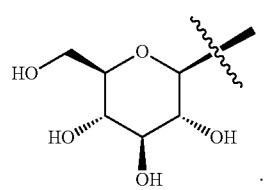

In some embodiments, R³ and R⁴ are both H. In some embodiments, R³ and R⁴ are both MeO. In some embodiments, one of R³ and R⁴ is H and the other of R³ and R⁴ is MeO.

In some embodiments, the compound of Formula I is selected from the group consisting of

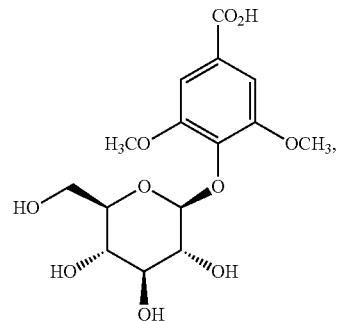

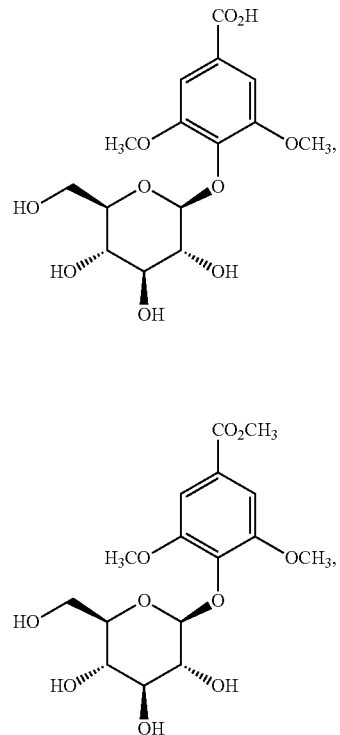

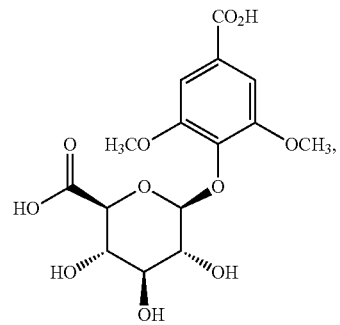

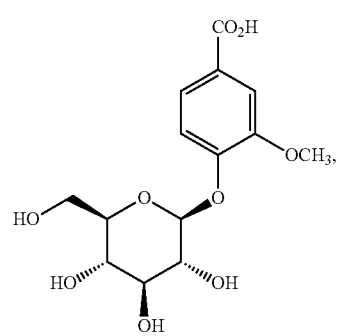

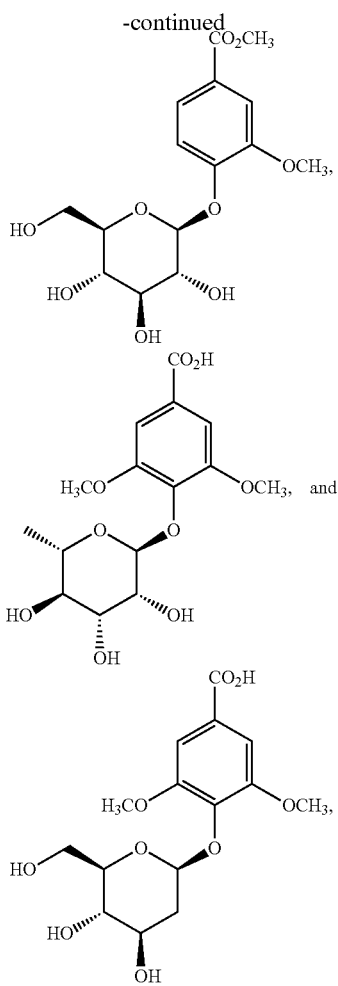

or a salt thereof.

In any of the embodiments described herein, the compound can be a substantially purified compound, for example, having a purity of at least 80%, at least 85%, at least 90%, at least 95%, or at least 99% by weight. In some embodiments, the compound can be a substantially purified compound having a purity of at least 80%, at least 85%, at least 90%, at least 95%, or at least 99% by HPLC measurement, for example, using the method described in the Examples section. In some embodiments, the compound can be a substantially purified compound having a purity by weight of about 80%, about 85%, about 90%, about 95%, about 99%, or any ranges between the specified values. In some embodiments, the compound can be a substantially purified compound having a purity by HPLC measurement of about 80%, about 85%, about 90%, about 95%, about 99%, or any ranges between the specified values.

In some embodiments, the compound of Formula I has an enantiomeric purity of about 80% ee or more, e.g., about 80% ee, about 85% ee, about 90% ee, about 91% ee, about 92% ee, about 93% ee, about 94% ee, about 95% ee, about 96% ee, about 97% ee, about 98% ee, about 99% ee, about 99.5% ee or more. Typically, the compound of Formula I has an enantiomeric purity of about 95% ee or more.

In some embodiments, the compound of Formula I is a beta-glycoside and is substantially free of an alpha-glycoside isomer, for example, the alpha-glycoside is less than 10% (e.g., less than 8%, less than 6%, less than 4%, less than 2%, or less than 1%) by weight.

The compound of Formula I as described herein (e.g., GSA) can be used in combination of various sweeteners. While not wishing to be bound by theories, it is believed that the compound of Formula I can enhance the sweet taste receptor through positive allosteric modulation of the receptor. For example, as discussed in the Examples section, GSA in a pure form was tested by human tasting and was found to be effective in increasing the overall sweetness of a nutritive sweetener (e.g., high-fructose corn syrup (HFCS)) sweetened beverages; decreasing the sweetness time-of-onset for high potency sweeteners such as rebaudioside A; decreasing bitter, metallic and licorice off-notes of high potency sweeteners (e.g., a 300 ppm solution of Rebaudioside A in phosphate buffer); and improving the sweet quality of sweetened beverages.

In various embodiments, the present disclosure provides a sweetener composition comprising a compound of Formula I and a sweetener. Suitable compounds of Formula I and sweeteners include any of those described herein.

Various amounts of the compound of Formula I (e.g., GSA) can be added to the sweetener composition to modify the sweetness profile of the sweetener. Any amount effective in modifying the sweetness profile of the sweetener can be included in the sweetener composition. For example, in some embodiments, the amount of the compound of Formula I can be included in the sweetener composition sufficient to decrease the sweetness time-of-onset, decrease bitter, metallic and licorice off-notes, and/or improve sweet quality (e.g., roundness) of the sweetener. In certain embodiments, the concentration of the compound of Formula I (e.g., GSA) in the sweetener composition can range from about 30 ppm to about 300 ppm (e.g., about 30 ppm, about 50 ppm, about 100 ppm, about 150 ppm, about 200 ppm, about 250 ppm, about 300 ppm, or any ranges between the recited values). In other embodiments, the concentration of the compound of Formula I can be at least 30 ppm (e.g., at least 50 ppm, at least 100 ppm, at least 150 ppm, at least 200 ppm, at least 250 ppm, or at least 300 ppm).

Various ratios of the compound of Formula I (e.g., GSA) to the sweetener are suitable for the sweetener composition described herein. For example, in some embodiments, the sweetener is a nutritive sweetener and the ratio of the compound of Formula I to the sweetener can range from about 1:400 to about 1:20 by weight, and in certain embodiments, from about 1:250 to about 1:50 by weight. In certain embodiments, the sweetener is a non-nutritive sweetener and the ratio of the compound of Formula I to the non-nutritive sweetener can be from about 3:1 to about 1:3 by weight, and in certain embodiments, from about 1.2:1 to about 1:1.2 by weight.

Sweetener

The sweeteners included in the sweetener compositions disclosed herein are edible consumables. The sweetener can be a nutritive or non-nutritive, natural or synthetic sweetener, or a combination of such sweeteners, so long as the sweetener or combination of sweeteners provides a taste which is perceived as sweet by the sense of taste. The perception of flavoring agents and sweetening agents can depend to some extent on the interrelation of elements. Flavor and sweetness can also be perceived separately, i.e., flavor and sweetness perception can be both dependent upon each other and independent of each other. For example, when a large amount of a flavoring agent is used, a small amount of a sweetening agent can be readily perceptible and vice versa. Thus, the oral and olfactory interaction between a flavoring agent and a sweetening agent can involve the interrelationship of elements.

When used to sweeten, the sweetener or combination of sweeteners in the sweetener composition is present in an amount above the sweeteners' sweetness recognition threshold concentration.

In certain embodiments, one or more nutritive sweeteners can be present in the sweetener composition in an amount of from about 1% to about 20% by weight of the sweetener composition, such as from about 3% to about 16% by weight, or from about 5% to about 12% by weight, depending upon the desired level of sweetness in the sweetener composition.

In certain embodiments, non-nutritive sweeteners can be present in the sweetener composition in an amount ranging from about 1 ppm to about 600 ppm (e.g., about 1 ppm, about 10 ppm, about 50 ppm, about 100 ppm, about 200 ppm, about 300 ppm, about 400 ppm, about 500 ppm, about 600 ppm, or any ranges between the recited values), depending upon the particular non-nutritive sweetener(s) being used and the desired level of sweetness in the sweetener composition.

Exemplary natural nutritive sweeteners suitable for use in the sweetener composition herein include crystalline or liquid sucrose, fructose, glucose, dextrose, maltose, trehalose, fructo-oligosaccharides, glucose-fructose syrup from natural sources such as apple, chicory, and honey; high fructose corn syrup, invert sugar, maple syrup, maple sugar, honey, brown sugar molasses, cane molasses, such as first molasses, second molasses, blackstrap molasses, and sugar beet molasses; sorghum syrup, and mixtures thereof.

Other sweeteners suitable for use in the sweetener composition herein include, but are not limited to, sugar alcohols such as erythritol, sorbitol, mannitol, xylitol, lactitol, isomalt, malitol, tagatose, trehalose, galactose, rhamnose, cyclodextrin, ribulose, threose, arabinose, xylose, lyxose, allose, altrose, mannose, idose, lactose, maltose, isotrehalose, neotrehalose, palatinose or isomaltulose, erythrose, deoxyribose, gulose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligosaccharides (gentiobiose, gentiotriose, gentiotetraose and the like), gal actooligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, and mixtures thereof.

Other sweeteners suitable for use in the sweetener composition herein include rare sugars such as D-allose, D-psicose (also known as D-allulose), L-ribose, D-tagatose, L-glucose, L-fucose, L-arabinose, D-turanose, D-leucrose, and mixtures thereof.

Exemplary artificial sweeteners suitable for use in the sweetener composition herein include, but are not limited to, saccharin, cyclamate, aspartame, neotame, advantame, acesulfame potassium, sucralose, mixtures thereof.

Exemplary natural non-nutritive potent sweeteners suitable for use in the sweetener composition herein include steviol glycosides (e.g., stevioside, steviolbioside, rebaudioside A, rebaudioside B, rebaudioside C, rebaudioside D, rebaudioside E, rebaudioside F, rebaudioside H, rebaudioside I, rebaudioside N, rebaudioside K, rebaudioside J, rebaudioside O, rebaudioside M, dulcoside A, rubusoside, iso-steviol glycosides such as iso-rebaudioside A, and mixtures thereof), Lo Han Guo powder, neohesperidin dihydrochalcone, trilobatin, glycyrrhizin, phyllodulcin, hernandulcin, osladin, polypodoside A, baiyunoside, pterocaryoside, thaumatin, monellin, monatin, mabinlins I and II, and mixtures thereof.

In other embodiments, Lo Han Guo juice concentrate can be used as a nutritive sweetener in the sweetener composition herein.

In some embodiments, the sweetener is selected from the group consisting of a steviol glycoside, *Stevia rebaudiana* extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and mixtures of any of them.

In some embodiments, the sweetener is a non-nutritive sweetener. In some embodiments, the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and combinations thereof. In some embodiments, the sweetener is aspartame, acesulfame potassium, steviol glycosides, or any combinations thereof.

Other suitable sweeteners that can be used in the sweetener composition herein are known in the art, for example, as described in WO 2016/040577 A1. In certain embodiments, combinations of one or more natural nutritive sweeteners, one or more artificial sweeteners, and/or one or more natural non-nutritive potent sweeteners can be used.

Sweetness Enhancer

In certain embodiments, the sweetener composition further comprises a sweetness enhancer.

In certain embodiments, the sweetness enhancer can be present at a concentration below its sweetness recognition threshold concentration. For example, and in certain embodiments, the sweetener composition can contain up to about 2 weight percent each of D-psicose, erythritol, or combination thereof. In some embodiments, D-psicose and/or erythritol can be present in an amount ranging from about 0.5 to about 2.0 weight percent. Alternatively, D-psicose can be present in an amount ranging from about 0.5 to about 2.0 weight percent and erythritol can be present in an amount ranging from about 0.5 to about 1 weight percent.

Suitable sweetness enhancers include any of those known in the art. Exemplary sweetness enhancers include, but are not limited to, D-psicose, erythritol, iso-rebaudioside A, rebaudioside B, rebaudioside C, rubusoside, trilobatin, phyllodulcin, brazzein, and/or mogrosides.

In some embodiments, the sweetness enhancer can be a rare sugar sweetness enhancer. Exemplary rare sugars include D-psicose (also referred to as D-allulose), D-allose, L-ribose, D-tagatose, L-glucose, L-fucose, L-arabinose, D-turanose, D-leucrose, and mixtures thereof.

In some embodiments, the sweetness enhancer can be a non-nutritive natural enhancer. Suitable non-nutritive natural enhancers include steviol glycosides. Suitable steviol glycosides, include, but are not limited to, stevioside, rebaudioside A, rebaudioside B, rebaudioside C, rebaudioside D, rebaudioside E, rebaudioside F, rebaudioside H, rebaudioside I, rebaudioside N, rebaudioside K, rebaudioside J, rebaudioside O, rebaudioside M, rubusoside, dulcoside A, iso-steviol glycosides such as iso-rebaudioside A, and mixtures thereof. In a particular embodiment, the sweetness enhancer can be rubusoside, rebaudioside C or rebaudioside B. In other embodiments, the non-nutritive natural sweetness enhancer can be a mogrol glycoside. Suitable mogrol glycosides, include, but are not limited to, mogroside V, isomogroside, mogroside IV, siamenoside, and mixtures thereof.

In some embodiments, the sweetness enhancer can be a sugar alcohol sweetness enhancer. Suitable sugar alcohols include erythritol, sorbitol, mannitol, xylitol, lactitol, isomalt, malitol, and mixture thereof.

In some embodiments, the sweetness enhancer can be a FEMA GRAS sweetness enhancers. Suitable FEMA GRAS enhancers include, but are not limited to, FEMA GRAS enhancer 4802, FEMA GRAS enhancer 4469, FEMA GRAS flavor 4701, FEMA GRAS enhancer 4720 (rebaudioside C), FEMA GRAS flavor 4774, FEMA GRAS enhancer 4708, FEMA GRAS enhancer 4728, FEMA GRAS enhancer 4601 (rebaudioside A) and combinations thereof.

In some embodiments, the sweetness enhancer is a salt based (e.g., NaCl) or benzoic acid based sweetness enhancer.

Other suitable sweetness enhancers are known in the art, for example, as described in WO 2016/040577 A1, in U.S. Patent Application Publication Nos. 2014/0271996, US 2014/0093630, 2014/0094453, and 2014/0272068, along with U.S. Pat. No. 8,877,922, all of which are incorporated by reference in their entireties.

Dry Blends/Tabletop Compositions

The sweetener composition described herein can be provided in various forms. In certain embodiments, the sweetener composition can be a dry blend comprising a compound of Formula I (e.g., GSA) and a nutritive sweetener. In some embodiments, the ratio of the compound of Formula I to nutritive sweetener in the dry blend can be from about 1:400 to about 1:20 by weight, and in certain embodiments, from about 1:250 to about 1:50 by weight. In certain embodiments, the compound of Formula I is GSA. Other suitable compounds of Formula I and suitable nutritive sweeteners are described herein.

In certain embodiments, the sweetener composition can also be a dry blend comprising a compound of Formula I (e.g., GSA) and a non-nutritive sweetener. In certain embodiments, the ratio of the compound of Formula I to the non-nutritive sweetener in the dry blend can be from about 3:1 to about 1:3 by weight, and in certain embodiments, from about 1.2:1 to about 1:1.2 by weight. In certain embodiments, the compound of Formula I is GSA. Other suitable compounds of Formula I and suitable non-nutritive sweeteners are described herein.

The dry blend sweetener composition can also contain one or more sweetness enhancers as discussed herein. Addition of a sweetness enhancer allows for a reduction in the amount of the amount of sweetener in the composition.

The dry blend sweetener composition can be a granular or powdered composition such as for use as a tabletop sweetener. Alternatively, the dry blend can be added to food products for baking or as a topping or to a liquid, such as to form a beverage from a powder e.g. chocolate milk, or Instant QUAKER Oats.

The dry blend sweetener composition can further include a binding or bulking agent, an anti-caking agents, and/or a flavor. Suitable binding or bulking agents include, but are not limited to maltodextrin; dextrose-maltodextrin blends, hydroxypropylmethyl cellulose, carboxymethyl cellulose, polyvinylpyrrolidone, and mixtures thereof. Suitable anti-caking agents include, but are not limited to alumino silicate, magnesium carbonate, and combinations thereof.

Aqueous Sweetener Compositions

In other embodiments, the sweetener composition can be provided in an aqueous formulation, the formulation comprising water, a sweetener, and a compound of Formula I. In certain embodiments, the compound of Formula I can be GSA. In certain embodiments, the sweetener is a nutritive sweetener, a non-nutritive sweetener, or a combination thereof. Other suitable compounds of Formula I and sweeteners are described herein. In certain embodiments, the aqueous formulation can further include a sweetener enhancer as described herein.

The sweetener composition described herein, whether a dry blend or in liquid form (e.g., aqueous form), can be utilized in any food or beverage product typically including a sweetener, including, but not limited to, those discussed throughout this disclosure. In some embodiments, the sweetener composition described herein is also suitable for use in cooking, baking (i.e. for use in cookies, cakes, pies, brownies, breads, granola bars, etc.), for preparing sweetened toppings, such as icings, and for use in jellies, jams, preserves, Instant QUAKER Oats, and the like. It is similarly suitable for use in frozen dairy products, such as ice cream, as well as in whipped toppings. Although in certain embodiments, the sweetener composition can be dissolved in the food or beverage, in other embodiments, the sweetener composition can be present in the food or beverage as part of a suspension or emulsion.

Beverage Products

In certain embodiments, the sweetener composition is provided in a beverage product. In some embodiments, the beverage product is a ready-to-drink beverage or a beverage concentrate. In some embodiments, the beverage product is a low-calorie or a zero-calorie beverage product.

Ready-to-Drink Beverages

Certain embodiments of the present disclosure are directed to ready-to-drink beverages comprising water, a sweetener composition comprising a sweetener and a compound of Formula I, and optionally an acidulant. In some embodiments, the acidulant is selected from the group consisting of phosphoric acid, citric acid, malic acid, tartaric acid, lactic acid, formic acid, ascorbic acid, fumaric acid, gluconic acid, succinic acid, maleic acid, adipic acid, and mixtures thereof.

In certain embodiments, the concentration of the compound of Formula I in the ready-to-drink beverage ranges from about 30 ppm to about 300 ppm (e.g., about 30 ppm, about 50 ppm, about 100 ppm, about 150 ppm, about 200 ppm, about 250 ppm, about 300 ppm, or any ranges between the recited values). In other embodiments, the concentration of the compound of Formula I in the ready-to-drink beverage can be at least 30 ppm (e.g., at least 50 ppm, at least 100 ppm, at least 150 ppm, at least 200 ppm, at least 250 ppm, or at least 300 ppm). In some embodiments, the compound of Formula I is GSA. Other suitable compounds of Formula I are described herein.

In certain embodiments, the ready-to-drink beverage comprises one or more nutritive sweeteners. In some embodiments, the one or more nutritive sweeteners can be present in the ready-to-drink beverage in an amount of from about 1% to about 20% by weight of the beverage composition, such as from about 3% to about 16% by weight, or from about 5% to about 12% by weight, depending upon the desired level of sweetness in the beverage.

In certain embodiments, the ready-to-drink beverage comprises a non-nutritive sweetener. In some embodiments, the non-nutritive sweetener can be present in the ready-to-drink beverage in an amount ranging from about 1 to about 600 ppm (e.g., about 1 ppm, about 10 ppm, about 50 ppm, about 100 ppm, about 200 ppm, about 300 ppm, about 400 ppm, about 500 ppm, about 600 ppm, or any ranges between the recited values), depending upon the particular non-nutritive sweetener(s) being used and the desired level of sweetness in the beverage.

The ready-to-drink beverage can further comprise one or more sweetness enhancers. In certain embodiments, the sweetness enhancer can be present at a concentration below its sweetness recognition threshold concentration. For example, and in certain embodiments, the ready-to-drink beverage can contain up to about 2 weight percent each of D-psicose, erythritol, or combination thereof. In some embodiments, D-psicose and/or erythritol can be present in an amount ranging from about 0.5 to about 2.0 weight percent. Alternatively, D-psicose can be present in an amount ranging from about 0.5 to about 2.0 weight percent and erythritol can be present in an amount ranging from about 0.5 to about 1 weight percent.

In certain embodiments, the ready-to-drink beverage can also include one or more salts. In other embodiments, salt concentration can range from about 100 ppm to about 1000 ppm, or in a further embodiment from about 200 ppm to about 800 ppm. In particular embodiments, the salt can be sodium chloride. In certain embodiments, the beverage composition can be completely or substantially salt free.

In certain embodiments, the ready-to-drink beverage can further comprise other ingredients such as antioxidants, food grade acids, and food grade bases. Other beverage components such as flavorants, colors, preservatives, carbon dioxide, buffering salts, and the like, can also be present.

In certain embodiments, the ready-to-drink beverages can be carbonated and non-carbonated soft drinks, fountain beverages, frozen ready-to-drink beverages, coffee, tea, and other brewed beverages, dairy beverages, flavored waters, enhanced waters, juices such as fruit juice (including diluted and ready to drink concentrated juices), fruit juice-flavored drinks, sport drinks, smoothies, functionally enhanced beverages such as caffeinated energy drinks, and alcoholic products. In particular embodiments, the beverage composition can be a cola beverage.

It should be understood that beverages and other beverage products in accordance with this disclosure can have any of numerous different specific formulations or constitutions. The formulation of a beverage product in accordance with this disclosure can vary, depending upon such factors as the product's intended market segment, its desired nutritional characteristics, flavor profile, and the like. For example, further ingredients can be added to the formulation of a particular beverage embodiment. Further ingredients include, but are not limited to, one or more additional sweeteners in addition to any sweetener already present, flavorings, electrolytes, vitamins, fruit juices or other fruit products, tastants, masking agents, flavor enhancers, carbonation, or any combination of the foregoing. These can be added to any of the beverage compositions to vary the taste, mouthfeel, and/or nutritional characteristics of the beverage composition.

In certain embodiments, a ready-to-drink beverage in accordance with this disclosure can comprise water, a sweetener, a compound of Formula I, an acidulant, and a flavoring. Exemplary suitable acidulants include, but are not limited to, phosphoric acid, citric acid, malic acid, tartaric acid, lactic acid, formic acid, ascorbic acid, fumaric acid, gluconic acid, succinic acid, maleic acid, adipic acid, and mixtures thereof. Exemplary flavorings include, but are not limited to, cola flavoring, citrus flavoring, spice flavorings, tea flavoring, coffee flavoring, juice flavoring, and combinations thereof. Carbonation in the form of carbon dioxide can be added for effervescence. In some embodiments, the water is carbonated water. In certain embodiments, preservatives can be added if desired or necessary, depending upon factors including the presence of other ingredients, production technique, desired shelf life, etc. In certain embodiments, caffeine can be added to the beverage. In certain embodiments, the beverage is substantially caffeine free (e.g., less than 1% by weight, less than 0.1% by weight, less than 0.01% by weight, less than 0.001% by weight, or less than 0.0001% by weight). In certain embodiments, the beverage is caffeine free. In some embodiments, the ready-to-drink beverage is a low-calorie or a zero-calorie beverage. In particular embodiments, the compound of Formula I is GSA. Other suitable compounds are described herein.

Certain exemplary embodiments of the beverages disclosed here are cola-flavored carbonated beverages, characteristically containing, in addition to the ingredients included in the beverage compositions disclosed herein, carbonated water, sweetener, kola nut extract and/or other flavorings, caramel coloring, phosphoric acid, and optionally other ingredients. Additional and alternative suitable ingredients will be recognized by those skilled in the art given the benefit of this disclosure.

Beverage Concentrates

Beverages are typically not prepared in large batches. Instead, a syrup (alternatively referred to as a beverage concentrate or concentrate), water, and optionally carbon dioxide are combined at the time of use or at the time of bottling or dispensing a beverage. The syrup is a concentrated solution of many of the soluble ingredients typically included in a given beverage.

Thus, in certain embodiments, the sweetener compositions described herein can be provided in a beverage concentrate. At least certain exemplary embodiments of the beverage concentrates contemplated can be prepared with an initial volume of water to which a sweetener and a compound of Formula I are added. In certain embodiments, ready-to-drink beverage compositions can be formed from the beverage concentrate by adding further volumes of water to the concentrate. In certain embodiments, a ready-to-drink beverage can be prepared from a concentrate by combining approximately 1 part concentrate with about 3 to about 7 parts water. In certain embodiments, the ready-to-drink beverage can be prepared by combining 1 part concentrate with 5 parts water. In certain exemplary embodiments the water added to the concentrate to form the ready-to-drink beverages can be carbonated.

The amounts of the compound of Formula I, sweetener and other ingredients present in the beverage concentrate are typically about 3 fold to about 7 fold of the respective amounts present in the ready-to-drink beverage as discussed herein. For example, in certain embodiments, the concentration of a compound of Formula I in the beverage concentrate can range from about 90 ppm to about 2100 ppm (e.g., about 90 ppm, about 200 ppm, about 400 ppm, about 600 ppm, about 800 ppm, about 1000 ppm, about 1200 ppm, about 1400 ppm, about 1600 ppm, about 1800 ppm, about 2000 ppm, about 2100 ppm, or any ranges between the recited values). In certain embodiments, the concentration of the compound of Formula I can be at least 90 ppm (e.g., at least 200 ppm, at least 400 ppm, at least 600 ppm, at least 800 ppm, at least 1000 ppm, at least 1200 ppm, at least 1400 ppm, at least 1600 ppm, at least 1800 ppm, at least 2000 ppm, or at least 2100 ppm).

Similarly, in certain embodiments, the beverage concentrate can comprise a nutritive sweetener at from about 6% to about 71% by weight of the beverage concentrate, such as from about 18% to about 62% by weight, or from about 30% to about 45% by weight, depending upon the desired level of sweetness for the ready-to-drink beverage.

In certain embodiments, the beverage concentrate can comprise non-nutritive sweetener at from about 6 ppm to about 3600 ppm depending upon the particular non-nutritive sweetener being used and the desired level of sweetness for the ready-to-drink beverage.

In certain embodiments, the syrups can further comprise a sweetness enhancers in an amount such that the concentration of the sweetness enhancer will be below its sweetness recognition threshold concentration in a ready-to-drink beverage.

For example, in certain embodiments, the syrup can contain up to about 18 weight percent of D-psicose, erythritol, or combination thereof. In other embodiments, D-psicose or erythritol can be present in an amount of from about 3 to about 9 weight percent. Alternatively, D-psicose can be present in an amount ranging from about 3 to about 9 weight percent and erythritol can be present in an amount of from about 3 to about 6 weight percent.

In certain embodiments, one or more salts can be included in the syrup. In certain embodiments the salt concentration in the syrup ranges from about 600 ppm to about 6000 ppm, and in certain embodiments, from about 1200 ppm to about 2400 ppm. In certain embodiments, the syrup can be completely or substantially salt free.

Water

Water is a basic ingredient in the aqueous compositions described herein (e.g., beverage products), typically being the vehicle or primary liquid portion in which the remaining ingredients are dissolved, emulsified, suspended or dispersed. Purified water can be used in the manufacture of certain embodiments of the beverages disclosed here, and water of a standard beverage quality can be employed in order not to adversely affect beverage taste, odor, or appearance. The water typically will be clear, colorless, free from objectionable minerals, tastes and odors, free from organic matter, low in alkalinity and of acceptable microbiological quality based on industry and government standards applicable at the time of producing the beverage.

In certain embodiments, water can be present at a level of from about 20 weight percent to about 99.9 weight percent in the aqueous compositions disclosed herein. In certain beverage embodiments, the quantity of water can range from about 80 weight percent to about 99.9 weight percent of the beverage. In at least certain exemplary embodiments the water used in beverages and concentrates disclosed here is "treated water," which refers to water that has been treated to reduce the total dissolved solids of the water prior to optional supplementation with calcium as disclosed in U.S. Pat. No. 7,052,725, which is incorporated by reference in its entirety.

Methods of producing treated water are known to those of ordinary skill in the art and include deionization, distillation, filtration and reverse osmosis ("r-o"), among others. The terms "treated water," "purified water,", "demineralized water," "distilled water," and "r-o water" are understood to be generally synonymous in this discussion, referring to water from which substantially all mineral content has been removed, typically containing no more than about 500 ppm total dissolved solids, e.g. 250 ppm total dissolved solids.

Food Products

The sweetener composition described herein can also be provided in a food product. In some embodiments, the present disclosure provides a food product comprising a food component and a sweetener composition comprising a sweetener and a compound of Formula I (e.g., GSA). In some embodiments, the food product is selected from the group consisting of oatmeal, cereal, baked goods, cookies, crackers, cakes, brownies, breads, snack foods, potato chips, tortilla chips, popcorn, snack bars, rice cakes, and grain-based food products. Suitable sweeteners and compounds of Formula I are described herein. Other suitable ingredients in the sweetener composition are also described herein.

Natural Embodiments

Certain embodiments of the described compositions can be "natural" in that they do not contain anything artificial or synthetic (including any color additives regardless of source) that would not normally be expected to be in the food or beverage. As used herein, therefore, a "natural" food or beverage product is defined in accordance with the following guidelines: Raw materials for a natural ingredient exists or originates in nature. Biological synthesis involving fermentation and enzymes can be employed, but synthesis with chemical reagents is not utilized. Artificial colors, preservatives, and flavors are not considered natural ingredients. Ingredients may be processed or purified through certain specified techniques including at least: physical processes, fermentation, and enzymolysis. Appropriate processes and purification techniques include at least: absorption, adsorption, agglomeration, centrifugation, chopping, cooking (baking, frying, boiling, roasting), cooling, cutting, chromatography, coating, crystallization, digestion, drying (spray, freeze drying, vacuum), evaporation, distillation, electrophoresis, emulsification, encapsulation, extraction, extrusion, filtration, fermentation, grinding, infusion, maceration, microbiological (rennet, enzymes), mixing, peeling, percolation, refrigeration/freezing, squeezing, steeping, washing, heating, mixing, ion exchange, lyophilization, osmose, precipitation, salting out, sublimation, ultrasonic treatment, concentration, flocculation, homogenization, reconstitution, enzymolysis (using enzymes found in nature). Processing aids (currently defined as substances used as manufacturing aids to enhance the appeal or utility of a food or beverage component, including clarifying agents, catalysts, flocculants, filter aids, and crystallization inhibitors, etc. See 21 CFR § 170.3(o)(24)) are considered incidental additives and may be used if removed appropriately.

Additional Ingredients

The food or beverage products disclosed herein can contain additional ingredients, for example, those typically included in food or beverage products.

In certain embodiments, the food or beverage products disclosed herein can contain a flavor composition, for example, natural, nature identical, and/or synthetic fruit flavors, botanical flavors, other flavors, and mixtures thereof. As used herein, the term "fruit flavor" refers generally to those flavors derived from the edible reproductive part of a seed plant including those plants wherein a sweet pulp is associated with the seed, e.g., tomato, cranberry, and the like, and those having a small, fleshy berry. The term berry includes true berries as well as aggregate fruits, i.e., not "true" berries, but fruit commonly accepted as such. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime grapefruit, tangerine, mandarin orange, tangelo, and pomelo, apple, grape, cherry, and pineapple flavors. In certain embodiments, the food or beverage products comprise a fruit flavor component, e.g., a juice concentrate or juice. As used here, the term "botanical flavor" refers to flavors derived from parts of a plant other than the fruit. As such, botanical flavors can include those flavors derived from essential oils and extracts of nuts, bark, roots, and leaves. Also included within the term "botanical flavor" are synthetically prepared flavors made to simulate botanical flavors derived from natural sources. Examples of such flavors include cola flavors, tea flavors, and mixtures thereof. The flavor component may further comprise a blend of several of the above-mentioned flavors. In certain exemplary embodiments of the beverage products, a cola flavor component is used or a tea flavor component. The particular amount of the flavor component useful for imparting flavor characteristics to the food or beverage products of the present disclosure will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression.

Juices suitable for use in certain exemplary embodiments of the food or beverage products disclosed herein include, e.g., fruit, vegetable and berry juices. Juices may be employed in the food or beverage products in the form of a concentrate, puree, single-strength juice, or other suitable forms. The term "juice" as used here includes single-strength fruit, berry, or vegetable juice, as well as concentrates, purees, milks, and other forms. Multiple different fruit, vegetable and/or berry juices can be combined, optionally along with other flavorings, to generate a concentrate or beverage having a desired flavor. Examples of suitable juice sources include plum, prune, date, currant, fig, grape, raisin, cranberry, pineapple, peach, banana, apple, pear, guava, apricot, Saskatoon berry, blueberry, plains berry, prairie berry, mulberry, elderberry, Barbados cherry (acerola cherry), choke cherry, date, coconut, olive, raspberry, strawberry, huckleberry, loganberry, currant, dewberry, boysenberry, kiwi, cherry, blackberry, quince, buckthorn, passion fruit, sloe, rowan, gooseberry, pomegranate, persimmon, mango, rhubarb, papaya, litchi, lemon, orange, lime, tangerine, mandarin, melon, watermelon, and grapefruit. Numerous additional and alternative juices suitable for use in at least certain exemplary embodiments will be apparent to those skilled in the art given the benefit of this disclosure. In the compositions of the present disclosure employing juice, juice can be used, for example, at a level of at least about 0.2 weight percent of the composition. In certain embodiments juice can be employed at a level of from about 0.2 weight percent to about 40 weight percent. In further embodiments, juice can be used, if at all, in an amounts ranging from about 1 weight percent to about 20 weight percent.

Juices that are lighter in color can be included in the formulation of certain exemplary embodiments to adjust the flavor and/or increase the juice content of the beverage without darkening the beverage color. Examples of such juices include apple, pear, pineapple, peach, lemon, lime, orange, apricot, grapefruit, tangerine, rhubarb, cassis, quince, passion fruit, papaya, mango, guava, litchi, kiwi, mandarin, coconut, and banana. Deflavored and decolored juices can be employed if desired.

Other flavorings suitable for use in at least certain exemplary embodiments of the food or beverage products disclosed here include, e.g., spice flavorings, such as cassia, clove, cinnamon, pepper, ginger, vanilla spice flavorings, cardamom, coriander, root beer, sassafras, ginseng, and others. Numerous additional and alternative flavorings suitable for use in at least certain exemplary embodiments will be apparent to those skilled in the art given the benefit of this disclosure. Flavorings may be in the form of an extract, oleoresin, juice concentrate, bottler's base, or other forms known in the art. In at least certain exemplary embodiments, such spice or other flavors complement that of a juice or juice combination.

The one or more flavorings may be used in the form of an emulsion. A flavoring emulsion can be prepared by mixing some or all of the flavorings together, optionally together with other ingredients of the food or beverage, and an emulsifying agent. The emulsifying agent can be added with or after the flavorings mixed together. In certain exemplary embodiments the emulsifying agent is water-soluble. Exemplary suitable emulsifying agents include gum acacia, modified starch, carboxymethylcellulose, gum tragacanth, gum ghatti and other suitable gums. Additional suitable emulsifying agents will be apparent to those skilled in the art of food or beverage formulations, given the benefit of this disclosure. The emulsifier in exemplary embodiments comprises greater than about 3% of the mixture of flavorings and emulsifier. In certain exemplary embodiments the emulsifier is from about 5% to about 30% of the mixture.

Carbon dioxide can be used to provide effervescence to certain exemplary embodiments of the food or beverage products disclosed here. Any of the techniques and carbonating equipment known in the art for carbonating beverages can be employed. Carbon dioxide can enhance beverage taste and appearance and may aid in safeguarding the beverage purity by inhibiting and/or destroying objectionable bacteria. In certain embodiments, for example, the beverage can have a $CO_2$ level up to about 4.0 volumes carbon dioxide. Other embodiments can have, for example, from about 0.5 volume to about 5.0 volumes of carbon dioxide. As used herein, one volume of carbon dioxide refers to the amount of carbon dioxide absorbed by a given quantity of a given liquid, such as water, at 60° F. (16° C.) and one atmospheric pressure. A volume of gas occupies the same space as does the liquid by which it is dissolved. The carbon dioxide content can be selected by those skilled in the art based on the desired level of effervescence and the impact of the carbon dioxide on the taste or mouthfeel of the beverage.

In certain embodiments, caffeine can be added to any of the food or beverage products described herein. The amount of caffeine added can be determined by the desired properties of a given beverage or syrup, and any applicable regulatory provisions of the country where the beverage or syrup is marketed. In certain embodiments caffeine can be included in an amount sufficient to provide a final beverage product having less than about 0.02 weight percent caffeine. The caffeine must be of purity acceptable for use in beverages. The caffeine may be natural or synthetic in origin.

The food or beverage products disclosed here can contain further additional ingredients, including, generally, any of those typically found in food or beverage formulations. Examples of such additional ingredients include, but are not limited to, caramel and other coloring agents or dyes, foaming or antifoaming agents, gums, emulsifiers, tea solids, cloud components, and mineral and non-mineral nutritional supplements. Examples of non-mineral nutritional supplement ingredients are known to those of ordinary skill in the art and include, for example, antioxidants and vitamins, including Vitamins A, D, E (tocopherol), C (ascorbic acid), B (thiamine), B2 (riboflavin), B6, B12, K, niacin, folic acid, biotin, and combinations thereof. The optional non-mineral nutritional supplements are typically present in amounts generally accepted under good manufacturing practices. Exemplary amounts can be between about 1% and about 100%, Recommended Daily Value (RDV), where such RDVs are established. In certain exemplary embodiments the non-mineral nutritional supplement ingredient(s) can be present in an amount of from about 5% to about 20% RDV, where established.

Preservatives may be used in at least certain embodiments of the food or beverage products disclosed here. That is, at least certain exemplary embodiments can contain an optional dissolved preservative system. Solutions with a pH below 4 and especially those below 3 typically are "microstable," i.e., they resist growth of microorganisms, and so are suitable for longer term storage prior to consumption without the need for further preservatives. However, an additional preservative system can be used if desired. If a preservative system is used, it can be added to the product at any suitable time during production, e.g., in some cases prior to the addition of sweeteners. As used here, the terms "preservation system" or "preservatives" include all suitable preservatives approved for use in beverage compositions, including, without limitation, such known chemical preservatives as benzoates, e.g., sodium, calcium, and potassium benzoate, sorbates, e.g., sodium, calcium, and potassium sorbate, citrates, e.g., sodium citrate and potassium citrate, polyphosphates, e.g., sodium hexametaphosphate (SHMP), and mixtures thereof, and antioxidants such as ascorbic acid, EDTA, BHA, BHT, TBHQ, dehydroacetic acid, dimethyldicarbonate, ethoxyquin, heptylparaben, and combinations thereof. Preservatives may be used in amounts not exceeding mandated maximum levels under applicable laws and regulations.

In the case of beverages in particular, the level of preservative used can be adjusted according to the planned final product pH and/or the microbiological spoilage potential of the particular beverage formulation. The maximum level employed typically is about 0.05 weight percent of the beverage. It will be within the ability of those skilled in the art, given the benefit of this disclosure, to select a suitable preservative or combination of preservatives for food or beverage products according to this disclosure.

Other methods of preservation suitable for at least certain exemplary embodiments of the products disclosed here include, e.g., aseptic packaging and/or heat treatment or thermal processing steps, such as hot filling and tunnel pasteurization. Such steps can be used to reduce yeast, mold and microbial growth in the beverage products. For example, U.S. Pat. No. 4,830,862 discloses the use of pasteurization in the production of fruit juice beverages as well as the use of suitable preservatives in carbonated beverages. U.S. Pat. No. 4,925,686 discloses a heat-pasteurized freezable fruit juice composition which contains sodium benzoate and potassium sorbate. Both of these patents are incorporated by reference in their entireties. In general, heat treatment includes hot fill methods typically using high temperatures for a short time, e.g., about 190° F. for 10 seconds, tunnel pasteurization methods typically using lower temperatures for a longer time, e.g., about 160° F. for 10-15 minutes, and retort methods typically using, e.g., about 250° F. for 3-5 minutes at elevated pressure, i.e., at pressure above 1 atmosphere.

Suitable antioxidants may be selected from the group consisting of rutin, quercetin, flavonones, flavones, dihydroflavonols, flavonols, flavandiols, leucoanthocyanidins, flavonol glycosides, flavonone glycosides, isoflavonoids, and neoflavonoids. In particular, the flavonoids may be, but not limited to, quercetin, eriocitrin, neoeriocitrin, narirutin, naringin, hesperidin, hesperetin, neohesperidin, neoponcirin, poncirin, rutin, isorhoifolin, rhoifolin, diosmin, neodiosmin, sinensetin, nobiletin, tangeritin, catechin, catechin gallate, epigallocatechin, epigallocatechin gallate, oolong tea polymerized polyphenol, anthocyanin, heptamethoxyflavone, daidzin, daidzein, biochaminn A, prunetin, genistin, glycitein, glycitin, genistein, 6,7,4' trihydroxy isoflavone, morin, apigenin, vitexin, balcalein, apiin, cupressuflavone, datiscetin, diosmetin, fisetin, galangin, gossypetin, geraldol, hinokiflavone, primuletin, pratol, luteolin, myricetin, orientin, robinetin, quercetagetin, and hydroxy-4-flavone.

Suitable food grade acids are water soluble organic acids and their salts and include, for example, phosphoric acid, sorbic acid, ascorbic acid, benzoic acid, citric acid, tartaric acid, propionic acid, butyric acid, acetic acid, succinic acid, glutaric acid, maleic acid, malic acid, valeric acid, caproic acid, malonic acid, aconitic acid, potassium sorbate, sodium benzoate, sodium citrate, amino acids, and combinations of any of them. Such acids are suitable for adjusting the pH of the food or beverage.

Suitable food grade bases are sodium hydroxide, potassium hydroxide, and calcium hydroxide. Such bases also are suitable for adjusting the pH of a food or beverage.

Method of Modulating Sweetness Profile

The compound of Formula I described herein can be used to modulate the sweetness profile of a sweetener. For example, as discussed in the Examples section, a compound of Formula I (GSA) was tested by human tasting and was found to be effective in increasing the overall sweetness of a nutritive sweetener (e.g., high-fructose corn syrup (HFCS)) sweetened beverages; decreasing the sweetness time-of-onset for high potency sweeteners such as rebaudioside A; decreasing bitter, metallic and licorice off-notes of high potency sweeteners (e.g., a 300 ppm solution of Rebaudioside A in phosphate buffer); and improving the sweet quality of sweetened beverages. Thus, the compound of Formula I (e.g., GSA) can be useful for improving the taste quality of a sweetener composition, for example, a sweetened beverage.

In some embodiments, the present disclosure provides a method of modulating the sweetness profile of a sweetener in a product. In some embodiments, the method comprises adding to the product a compound of Formula I. In some embodiments, the product can be either a beverage product (e.g., a ready-to-drink beverage or a beverage concentrate) or a food product. Suitable compounds of Formula I and sweeteners include any of those described herein. For example, in some embodiments, the compound of Formula I is GSA. In some embodiments, the sweetener is high-fructose corn syrup. In some embodiments, the sweetener is rebaudioside A.

Any effective amount of the compound of Formula I can be added to the product to modulate the sweetness profile of the sweetener. For example, the compound of Formula I can be added in an amount sufficient to increase the overall sweetness, decrease the sweetness time-of-onset, decrease bitter, metallic and licorice off-notes, and/or improve sweet quality (e.g., roundness) of the sweetener. In certain embodiments, the compound of Formula I (e.g., GSA) can be added in an amount to achieve a concentration in the product ranging from about 30 ppm to about 300 ppm (e.g., about 30 ppm, about 50 ppm, about 100 ppm, about 150 ppm, about 200 ppm, about 250 ppm, about 300 ppm, or any ranges between the recited values). In other embodiments, the compound of Formula I can be added in an amount to achieve a concentration in the product of at least 30 ppm (e.g., at least 50 ppm, at least 100 ppm, at least 150 ppm, at least 200 ppm, at least 250 ppm, or at least 300 ppm).

In some embodiments, the method comprises adding the compound of Formula I (e.g., GSA) in an effective amount to improves the overall sweetness of the product. In some embodiments, the product is a sweetened beverage comprising a nutritive sweetener. In some embodiments, the nutritive sweetener is high-fructose corn syrup (HFCS). In some embodiments, the compound of Formula I (e.g., GSA) is added in an amount to achieve a concentration in the product ranging from about 30 ppm to about 300 ppm (e.g., about 30 ppm to about 100 ppm). In some embodiments, the compound of Formula I (e.g., GSA) is added in an effective amount to improve the overall sweetness of the product by about 10%, about 20%, about 30%, or about 40% compared to that of the product before adding the compound of Formula I. In some embodiments, the compound of Formula I is GSA, and the method comprises adding GSA in a sufficient amount to increase the overall sweetness of a 6% HFCS solution so that it tasted as sweet as an 8% HFCS solution. In other words, adding GSA improves the overall sweetness by about 33%. In some embodiments, the GSA is added in an amount to achieve a concentration in the product ranging from about 30 ppm to about 100 ppm.

In some embodiments, the method comprises adding the compound of Formula I (e.g., GSA) in an effective amount to decrease the sweetness time-of-onset of a sweetener in the product. In some embodiments, the sweetener is a high potency sweetener such as steviol glycoside, for example, rebaudioside A. In some embodiments, the compound of Formula I (e.g., GSA) is added in an amount to achieve a concentration in the product ranging from about 30 ppm to about 300 ppm (e.g., about 30 ppm to about 100 ppm). In some embodiments, the sweetener (e.g., rebaudioside A) is present in the product in a concentration from about 1 ppm to about 600 ppm (e.g., about 300 ppm). In particular embodiments, the method comprises adding the compound of Formula I (e.g., GSA) in an effective amount to shorten the sweetness time-of-onset of the product. In some embodiments, the product is a beverage product comprising about 300 ppm of a steviol glycoside such as rebaudioside A.

In some embodiments, the method comprises adding the compound of Formula I (e.g., GSA) in an effective amount to decrease bitter, metallic and/or licorice off-notes of the product. In other embodiments, the method comprises adding the compound of Formula I (e.g., GSA) in an effective amount to improve the sugar-like roundness of the product. In some embodiments, the product is a beverage product. In some embodiments, the sweetener is a high potency sweetener such as steviol glycoside, for example, rebaudioside A. In some embodiments, the compound of Formula I (e.g., GSA) is added in an amount to achieve a concentration in the product ranging from about 30 ppm to about 300 ppm (e.g., about 30 ppm to about 100 ppm). In some embodiments, the sweetener (e.g., rebaudioside A) is present in the product in a concentration from about 1 ppm to about 600 ppm (e.g., about 300 ppm). In particular embodiments, the method comprises adding GSA in an amount to achieve a concentration in the product ranging from about 30 ppm to about 300 ppm. In some embodiments, the beverage product comprises about 300 ppm of a steviol glycoside such as rebaudioside A.

Method of Synthesizing GSA Analogs

Compounds of Formula I described herein can be obtained by various methods. For example, in some embodiments, compounds of Formula I can be chemically synthesized using methods known to those skilled in the art in view of this disclosure, or by the illustrative methods shown in Method 1 below. Suitable protecting groups can be employed in the synthesis, if needed. See Wuts, P. G. M.; Greene, T. W., "Greene's Protective Groups in Organic Synthesis", 4th Ed., J. Wiley & Sons, NY, 2007.

Method 1

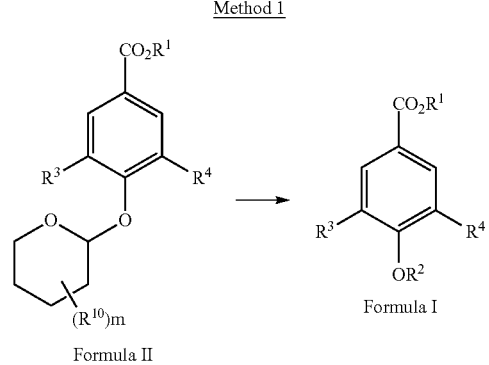

wherein $R^1$, $R^2$, $R^3$, and $R^4$ are defined herein;

wherein

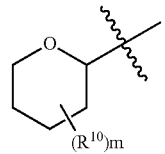

represents a protected residue of a pyranoside selected from the group consisting of glucopyranoside, glucuronopyranoside, rhamnopyranoside, galactopyranoside, deoxyglucopyranoside, and mannopyranoside.

In general, compounds of Formula I can be formed by removing the protecting groups from Formula II. In some embodiments, Formula II contains one or more ester bonds, for example, $R^1$ in Formula II is methyl or ethyl, and the deprotecting step also hydrolyzes the one or more esters (e.g., methyl or ethyl ester) into carboxylic acids, for example, $R^1$ in Formula I is H. In some embodiments, Formula II contains one or more ester bonds, for example, $R^1$ in Formula II is methyl or ethyl, and the deprotecting step is followed by a further hydrolysis step to convert the one or more esters (e.g., methyl or ethyl ester) into carboxylic acids, for example, $R^1$ in Formula I is H. In some embodiments, the respective $R^1$, $R^3$, and $R^4$ in Formula I and Formula II are the same and no ester hydrolysis is necessary.

The protecting groups for the pyranoside portion in Formula II can be any groups suitable for protecting a pyranose. Such protecting groups are generally known in the art. In some embodiments, the protecting group can be an actyl group. For example, in some embodiments, in Formula II can be

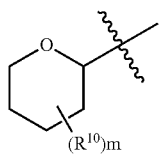

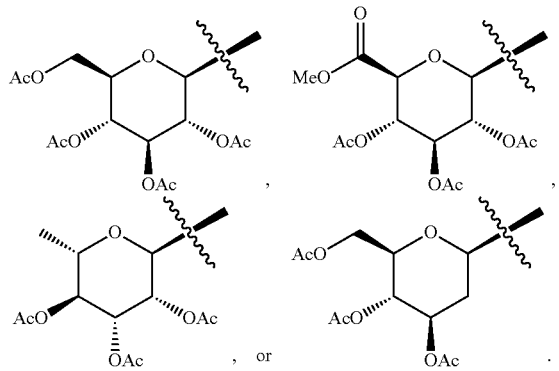

Compounds of Formula II can be prepared by various methods. In some embodiments, compounds of Formula II can be prepared by reacting a compound of Formula III with a compound of Formula IV.

Method 2

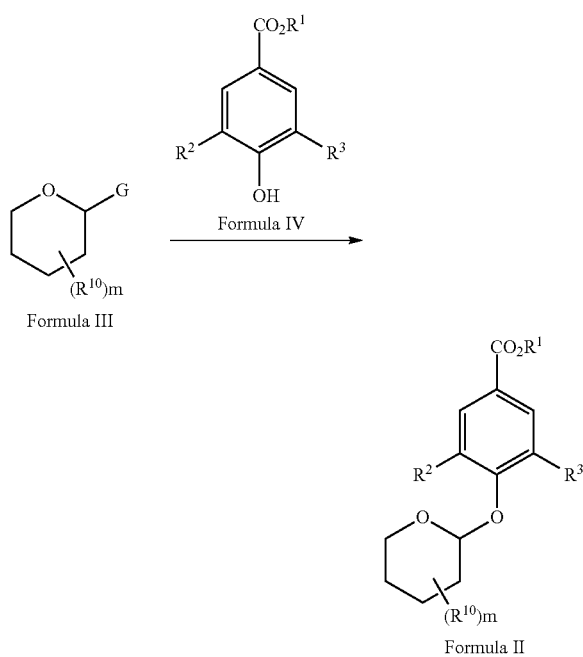

wherein $R^1$, $R^2$, $R^3$, $R^{10}$ and G are defined herein.

In general, Formula III is an activated pyranoside, which can react with a compound of Formula IV to form a glycoside bond. For example, G in Formula III can be a leaving group. Various ways of activating a pyranose for glycoside formation are known in the art. For example, in some embodiments, G in Formula III can be

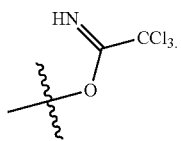

Some exemplary methods are described in the Examples section.

The glycoside formation discussed herein is generally performed in the presence of a Lewis acid, such as $BF_3OEt_2$. Other suitable reaction conditions are known to those skilled in the art and can be used in embodiments described herein.

EMBODIMENTS

In addition to the various embodiments described above, the present disclosure includes the following specific embodiments numbered E1 through E53. This list of embodiments is presented as an exemplary list and the application is not limited to these embodiments.

E1. A sweetener composition comprising a sweetener and a compound having a structure according to Formula I:

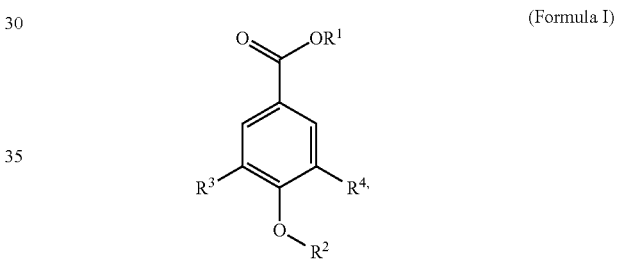

(Formula I)

wherein $R^1$ is H, Me, or Et, $R^2$ is a pyranoside selected from the group consisting of glucopyranoside, glucuronopyranoside, rhamnopyranoside, galactopyranoside, deoxyglucopyranoside, and mannopyranoside; and $R^3$ and $R^4$ are each independently H or MeO, or a salt thereof.

E2. The sweetener composition of E1, wherein $R^1$ is H.

E3. The sweetener composition of E1, wherein $R^1$ is Me.

E4. The sweetener composition of any one of E1-E3, wherein one of $R^3$ and $R^4$ is MeO.

E5. The sweetener composition of any one of E1-E4, wherein both $R^3$ and $R^4$ are MeO.

E6. The sweetener composition of any one of E1-E5, wherein $R^2$ is a beta-pyranoside.

E7. The sweetener composition of any one of E1-E6, wherein $R^2$ is a D-pyranoside.

E8. The sweetener composition of any one of E1-E7, wherein $R^2$ is a beta-D-glucopyranoside.

E9. The sweetener composition of E1, wherein the compound is selected from the group consisting of

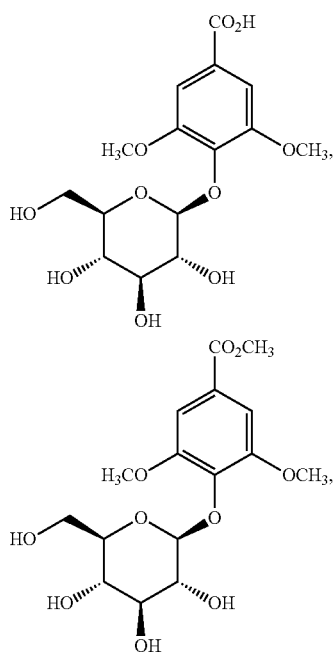

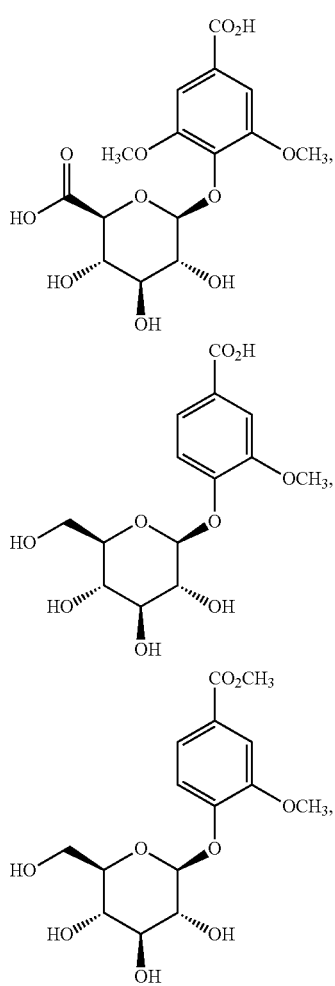

-continued and any combination thereof,
or a salt thereof.

E10. The sweetener composition of E1, wherein the compound is or a salt thereof.

E11. The sweetener composition of any one of E1-E10, wherein the sweetener is selected from the group consisting of a steviol glycoside, *Stevia rebaudiana* extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and any mixture thereof.

E12. The sweetener composition of any one of E1-E10, wherein the sweetener is a non-nutritive sweetener.

E13. The sweetener composition of E12, wherein the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and any combination thereof.

E14. The sweetener composition of E12, wherein the sweetener is aspartame, acesulfame potassium, steviol glycosides, or any combination thereof.

E15. The sweetener composition of any one of E1-E14, further comprising a sweetness enhancer.

E16. The sweetener composition of E15, wherein the sweetness enhancer is selected from the group consisting of D-psicose, erythritol, rubusoside, rebaudioside B, rebaudioside C, trilobatin, phyllodulcin, brazzein, mogrosides, and any combination thereof.

E17. The sweetener composition of any one of E1-E16, wherein the sweetener composition is a tabletop sweetener composition.

E18. The sweetener composition of any one of E1-E16, wherein the sweetener composition is an aqueous sweetener composition.

E19. The sweetener composition of any one of E1-E18, wherein the compound is present in the sweetener composition in a concentration ranging from about 30 ppm to about 300 ppm.

E20. A beverage product comprising a sweetener composition of any one of E1-E19.

E21. The beverage product of E20, wherein the beverage product is a ready-to-drink beverage.

E22. The beverage product of E20, wherein the beverage product is a beverage concentrate.

E23. A ready-to-drink beverage comprising:
a) water;
b) a sweetener composition of any one of E1-E19; and
c) optionally an acidulant selected from the group consisting of phosphoric acid, citric acid, malic acid, tartaric acid, lactic acid, formic acid, ascorbic acid, fumaric acid, gluconic acid, succinic acid, maleic acid, adipic acid, and any mixture thereof.

E24. The ready-to-drink beverage of E23, wherein the water is carbonated water.

E25. The ready-to-drink beverage of E23 or E24, further comprising a cola flavorant.

E26. The ready-to-drink beverage of any one of E23-E25, wherein the acidulant is phosphoric acid.

E27. The ready-to-drink beverage of any one of E23-E25, further comprising a tea flavorant.

E28. The ready-to-drink beverage of any one of E23-E25, further comprising a coffee flavorant.

E29. The ready-to-drink beverage of any one of E23-E28, further comprising caffeine.

E30. The ready-to-drink beverage of any one of E23-E28, which is substantially caffeine free.

E31. The ready-to-drink beverage of any one of E23-E30, wherein the beverage is a low-calorie or zero-calorie beverage.

E32. The ready-to-drink beverage of E23, wherein the beverage is selected from the group consisting of carbonated beverages, non-carbonated beverages, fountain beverages, frozen carbonated beverages, fruit juices, fruit juice-flavored drinks, fruit-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and any mixture thereof.

E33. A food product comprising a food component and a sweetener composition of any one of E1-E19.

E34. The food product of E33, wherein the food product is selected from the group consisting of oatmeal, cereal, baked goods, cookies, crackers, cakes, brownies, breads, snack foods, potato chips, tortilla chips, popcorn, snack bars, rice cakes, and grain-based food products.

E35. A method of modulating sweetness profile of a sweetener in a product, comprising adding to the product a compound having a structure according to Formula I:

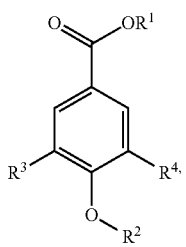

(Formula I)

wherein $R^1$ is H, Me, or Et, $R^2$ is a pyranoside selected from the group consisting of glucopyranoside, glucuronopyranoside, rhamnopyranoside, galactopyranoside, deoxyglucopyranoside, and mannopyranoside; and $R^3$ and $R^4$ are each independently H or MeO, or a salt thereof.

E36. The method of E35, wherein $R^1$ is H.

E37. The method of E35, wherein $R^1$ is Me.

E38. The method of any one of E35-E37, wherein one of $R^3$ and $R^4$ is MeO.

E39. The method of any one of E35-E38, wherein both $R^3$ and $R^4$ are MeO.

E40. The method of any one of E35-E39, wherein $R^2$ is a beta-pyranoside.

E41. The method of any one of E35-E40, wherein $R^2$ is a D-pyranoside.

E42. The method of any one of E35-E41, wherein $R^2$ is a beta-D-glucopyranoside.

E43. The method of E35, wherein the compound is selected from the group consisting of

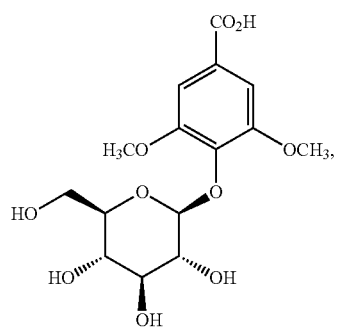

-continued

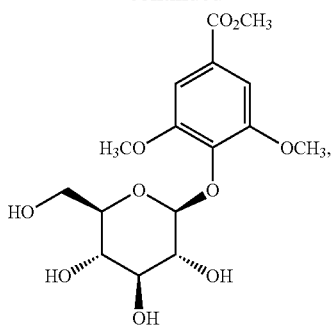 [SMILES: COc1cc(C(=O)O)cc(OC)c1O[C@@H]1O[C@H](CO)[C@@H](O)[C@H](O)[C@H]1O]

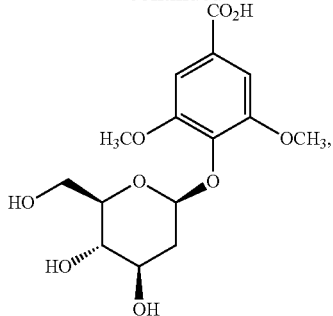

and any combination thereof,
or a salt thereof.

E44. The method of E35, wherein the compound is

or a salt thereof.

E45. The method of any one of E35-E44, wherein the compound is added in an amount to achieve a concentration in the product ranging from about 30 ppm to about 300 ppm.

E46. The method of E45, wherein the sweetener is selected from the group consisting of a steviol glycoside, *Stevia rebaudiana* extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and any mixture thereof.

E47. The method of E45, wherein the sweetener is a non-nutritive sweetener.

E48. The method of E45, wherein the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and any combination thereof.

E49. The method of any one of E35-E48, wherein the product is a beverage product.

E50. The method of E49, wherein the beverage product is selected from the group consisting of carbonated beverages, non-carbonated beverages, fountain beverages, frozen carbonated beverages, powdered concentrates, beverage concentrates, fruit juices, fruit juice-flavored drinks, fruit-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and any mixture thereof.

E51. The method of any one of E35-E48, wherein the product is a food product.

E52. The method of E51, wherein the food product is selected from the group consisting of oatmeal, cereal, baked goods, cookies, crackers, cakes, brownies, breads, snack foods, potato chips, tortilla chips, popcorn, snack bars, rice cakes, and grain-based food products.

E53. A compound selected from the group consisting of:

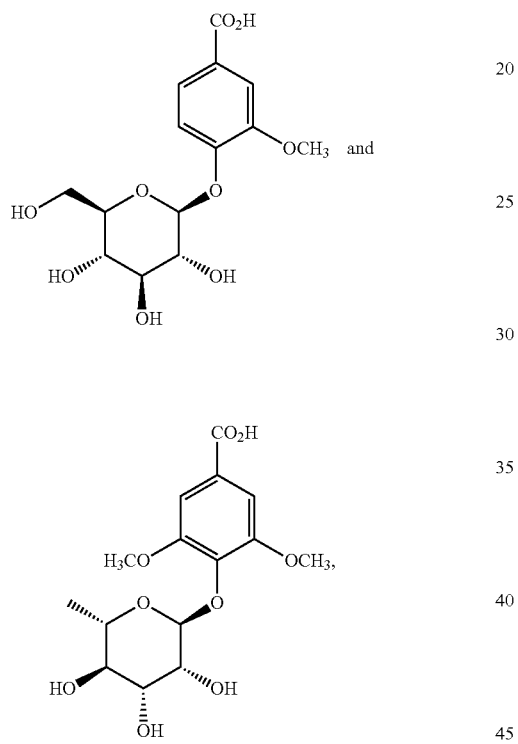

or a salt thereof.

EXAMPLES

1H NMR were run on a Varian 400 MHz NMR machine at room temperature at a concentration of ca. 1-3 mg/mL of solvent. Deuterated DMSO or methanol were typically used as the solvent.

HPLC method: Water and acetonitrile containing 0.1-0.5% TFA were used as solvents with a flow rate of 0.5-1.0 mL/min and a typical eluent gradient of 10-100% acetonitrile over 4.5 minutes at 40° C. The column was typically a C18 reversed-phase column such as the Xbridge Shield RP18 2.1×50 mm column using 5 μM sized silica gel. The analytes were identified using UV detection at 210 nm. Alternatively, MS was used as a detection method.

MS method: Samples were ionized using ES-API method on an Agilent LC/MS. Detection was run in positive ion mode.

Example 1. Synthesis and Characterization of GSA Analogs

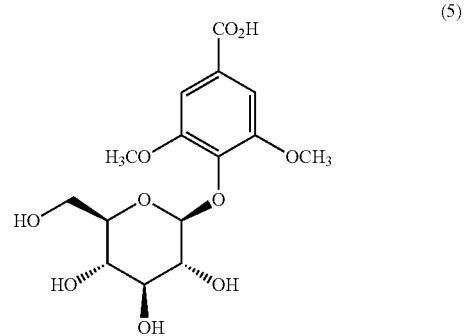

(5)

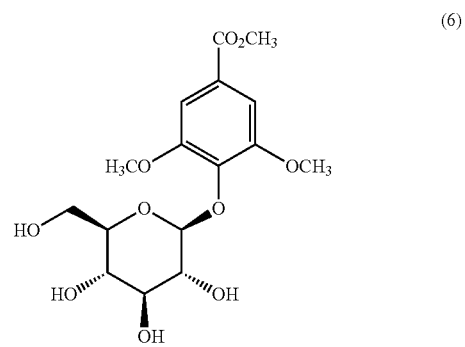

(6)

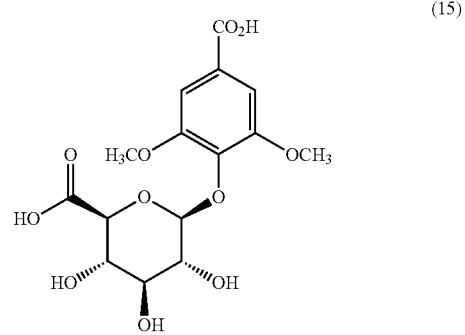

(15)

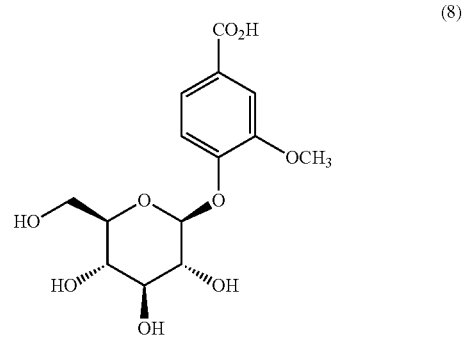

(8)

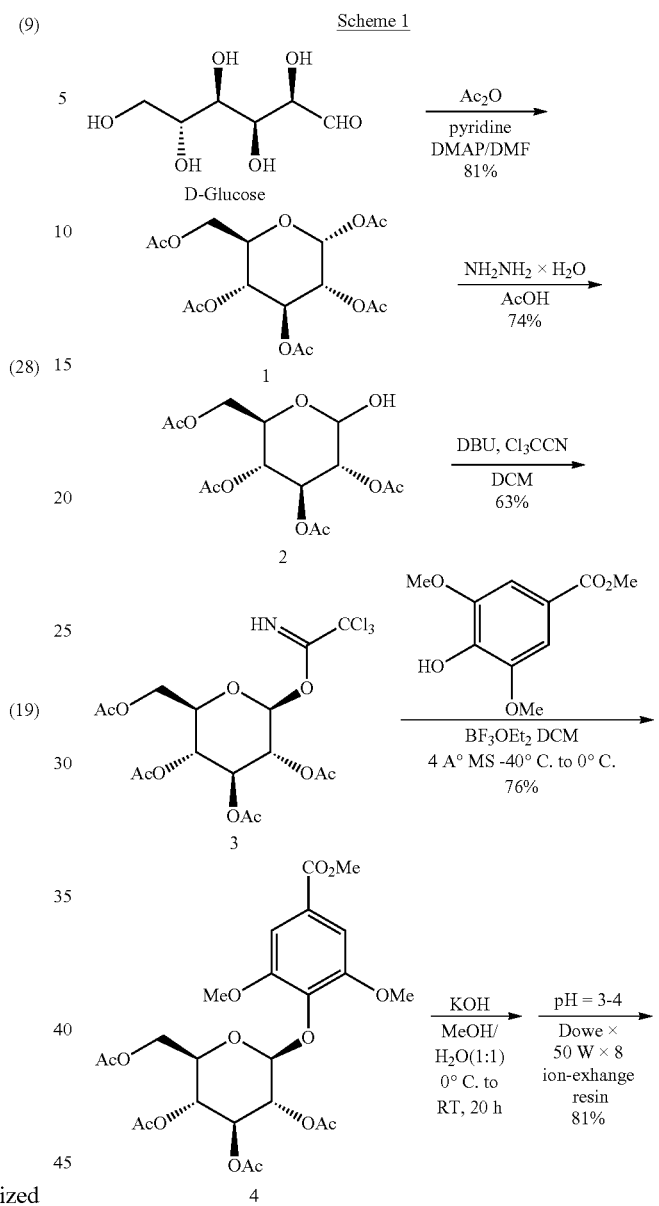

Scheme 1

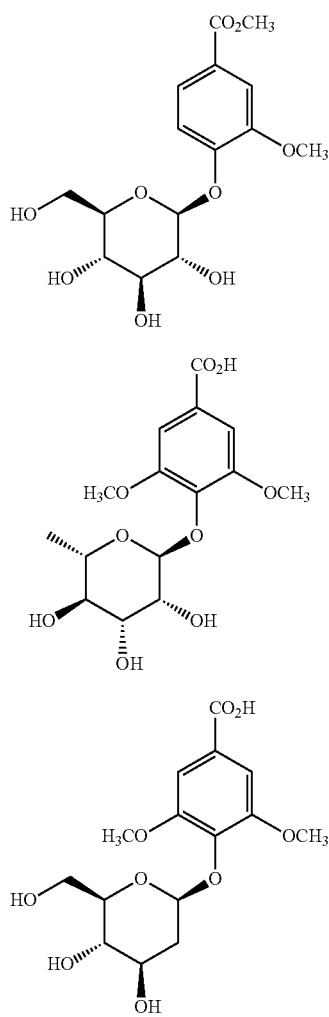

Example 1A. Syringic acid 4-O-β-D-glucoside

Syringic acid 4-O-β-D-glucoside 5, has been synthesized from D-glucose in approximately 32% overall yield via the chemistry illustrated in Scheme 1.

The experimental procedure of intermediates (1-4) in Scheme 1 are described.

(2R,3R,4S,5R,6R)-6-(acetoxymethyl)tetrahydro-2H-pyran-2,3,4,5-tetrayl tetraacetate (1)

To a solution of D-glucose (CAS#50-99-7, 36.04 g, 0.2 mol) in anhydrous DMF (80 mL) was added sequentially acetic anhydride (188 mL), pyridine (162 mL, 2 mol), and DMAP (1.22 g, 0.01 mmol). The reaction mixture was stirred at ambient temperature for 3 h and quenched by dilution with water. The aqueous phase was extracted with ethyl acetate (2×300 mL) and the organic phase was washed with 1 N HCl (2×150 mL) and water. The organic layer was washed with saturated aq NaCl, dried over MgSO$_4$ and concentrated. Recrystalization of the crude product from ethanol (400 mL) gave [(2R,3R,4S,5R)-3,4,5,6-tetrakis (acetyloxy)oxan-2-yl]methyl acetate as a white solid (63 g, 81%) white solid.

(2R,3R,4S,5R)-2-(acetoxymethyl)-6-hydroxytetrahydro-2H-pyran-3,4,5-triyl triacetate (2)

A solution of [(2R,3R,4S,5R)-3,4,5,6-tetrakis(acetyloxy) oxan-2-yl]methyl acetate (50 g, 128.1 mmol) in THF (150 mL) was treated with acetic acid (8.07 mL, 140.9 mmol) and hydrazine monohydrate (7.05 g, 140.9 mmol). The temperature of reaction mixture was slightly exothermic while addition of hydrazine (24° C. to 33° C.). The reaction mixture was stirred at ambient temperature for 4 h and extracted with ethyl acetate (400 mL). The organic phase was washed with water (300 mL), dried over MgSO$_4$, and concentrated to give crude glucose tetraacetate as a off-white solid (43 g). Purification using a short pad of silica gel gave [(2R,3R,4S,5R)-3,4,5-tris(acetyloxy)-6-hydroxyoxan-2-yl] methyl acetate yield 33 g (74%). (Note: In a pilot reaction, this was used in the next step without further purification).

(2R,3R,4S,5R,6S)-2-(acetoxymethyl)-6-(2,2,2-trichloro-1-iminoethoxy)tetrahydro-2H-pyran-3,4,5-triyl triacetate (3)

While under nitrogen, a solution of [(2R,3R,4S,5R)-3,4, 5-tris(acetyloxy)-6-hydroxyoxan-2-yl]methyl acetate (32 g, 91.87 mmol) in dichloromethane (100 mL) was treated with trichloroacetontrile (53.06 mL, 367.5 mmol) and 1,8-diazabicyclo[5,4,0] undec-ene (DBU, 1.1 mL) at 0° C. After stirring overnight, the crude product was concentrated and purified by flash column chromatography on silica gel (50% EtOAc in hexanes) to give a [(2R,3R,4S,5R)-3,4,5-tris (acetyloxy)-6-[(trichloroethanimidoyl)oxy]oxan-2-yl] methyl acetate 33 g (73%) as a sticky clear oil.

(2R,3R,4S,5R,6S)-2-(acetoxymethyl)-6-(2,6-dimethoxy-4-(methoxycarbonyl)phenoxy)tetrahydro-2H-pyran-3,4,5-triyl triacetate (4)

While under nitrogen, methyl syringate (2.153 g, 10.15 mmol), [(2R,3R,4S,5R)-3,4,5-tris(acetyloxy)-6-[(trichloroethanimidoyl)oxy]oxan-2-yl]methyl acetate (6 g, 12.18 mmol), in anhydrous dichloromethane (80 mL) with 4 A molecular sieves was stirred for 1 h at room temperature, cooled to −40° C. and treated with BF$_3$OEt$_2$ (0.372 mL, 2.9 mmol) After stirring for 15 min, the solution was warmed to 0° C. After 2 h the reaction mixture was quenched with Et$_3$N (3-4 drops), diluted with dichloromethane, filtered, and concentrated. Purification using flash column chromatography (40% EtOAc in hexanes) gave methyl 3,5-dimethoxy-4-{[(2S,3R,4S,5R,6R)-3,4,5-tris(acetyloxy)-6-[(acetyloxy) methyl]oxan-2-yl]oxy}benzoate (4.2 g, 76%) as a light foam solid.

Syrigic Acid 4-O-β-D-glucoside (5)

An ice-cooled solution of methyl 3,5-dimethoxy-4-{[(2S, 3R,4S,5R,6R)-3,4,5-tris(acetyloxy)-6-[(acetyloxy)methyl] oxan-2-yl]oxy}benzoate (1.4 g, 2.58 mmol) in methanol (30 mL) was treated with aq KOH (1.303 g, 23 mmol dissolved in 30 mL of water). After the addition was complete, the mixture was stirred at room temperature for 16 h and neutralised with Dowex 50Wx8 ion-exchange resin (ca. 7 g), adjusting to pH=7 to capture the product. The resin solution was acidification to release the product (pH=3-4), filtrated through Celite and concentrated to give the fully deprotected crude 3,5-dimethoxy-4-{[(2S,3R,4S,5S,6R)-3,4,5-trihydroxy-6-(hydroxymethyl)oxan-2-yl]oxy}benzoic acid as a white solid (950 mg, >100%). Purification by preparative HPLC (CH$_3$CN/water, gradient mobile phase, 40 mL/min) followed by lyophilization (Freeze-dry method) gave the target compound 0.75 g (81%) as a white solid. LC/MS, 378.2, 388.3. $^1$H NMR of compound (5) is shown in FIG. 1.

Example 1B. Methyl Syringate 4-O-β-D-glucoside

Figure 2:
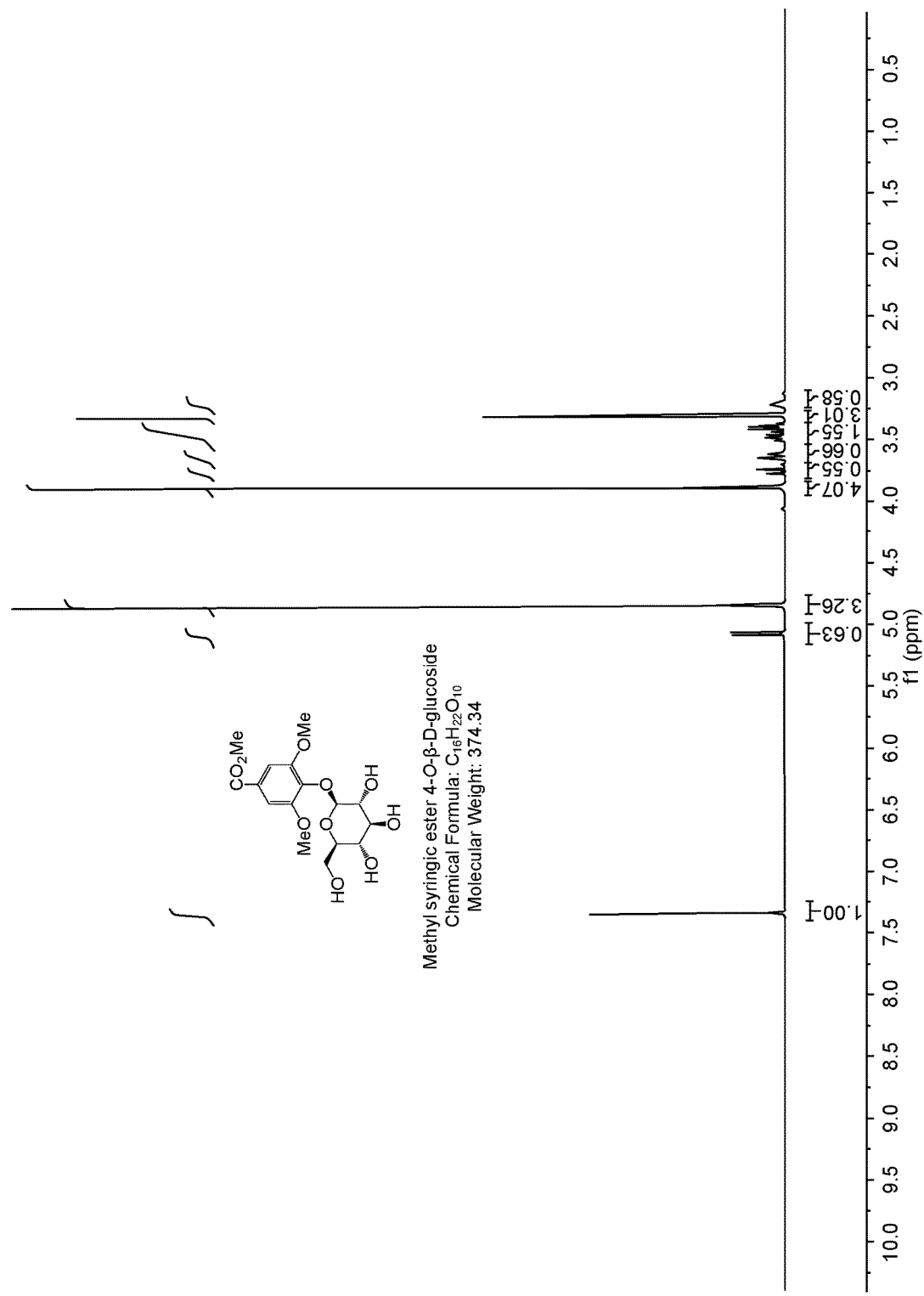

To a solution of methyl 3,5-dimethoxy-4-{[(2S,3R,4S,5R, 6R)-3,4,5-tris(acetyloxy)-6-[(acetyloxy)methyl]oxan-2-yl] oxy}benzoate (800 mg, 1.48 mmol) in THF/CH$_3$OH (40 mL; v/v=1/1) was added K$_2$CO$_3$ (20.38 mg, 0.148 mmol). The resulting suspension was stirred at rt for 2 hr and then filtered through a pad of Celite. The filtrate was concentrated under reduced pressure to give crude product as a white solid. Methyl syringate 4-O-β-D-glucoside, 6, was isolated from preparative HPLC (10% CH$_3$CN in water) as a white solid (450 mg, 81%). LC/MS, 397.1, 392.3. $^1$H NMR of compound (6) is shown in FIG. 2.

Example 1C. Vanillic Acid 4-O-beta-D-glucoside

According to the preparation in Scheme 1, vanillic acid 4-O-beta-D-glucoside (8) was synthesized from intermediate 3 (Scheme 2)

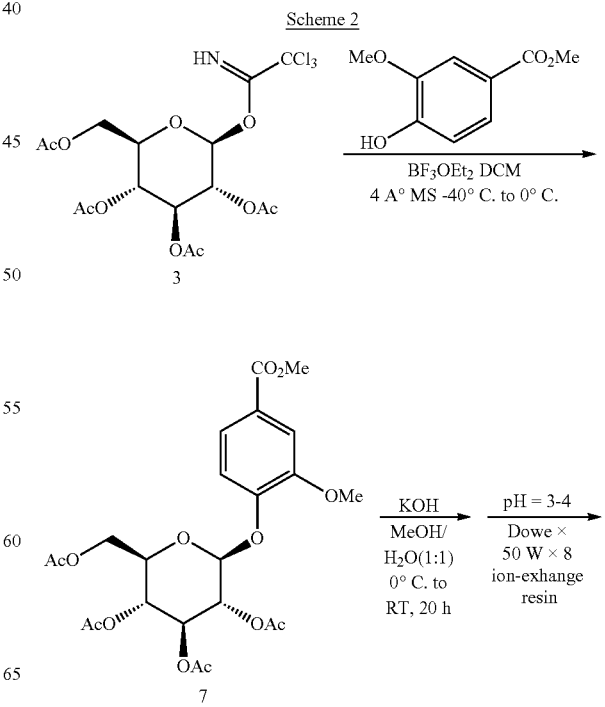

Scheme 2

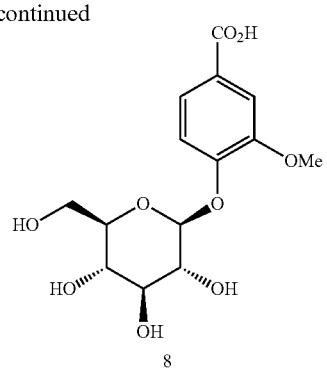

(2R,3R,4S,5R,6S)-2-(acetoxymethyl)-6-(2-methoxy-4-methoxycarbonyl)phenoxy) tetrahydro-2H-3,4,5-triyl triacetate (7)

Methyl vanillate (1.078 g, 5.92 mmol), [(2R,3R, 4S, 5R)-3,4,5-tris(acetoxy)-6-[(trichloroethanimidoyl)oxy] oxan-2-yl]methyl acetate (3.5 g, 7.104 mmol), and 4 Å molecular sieves were stirred in anhydrous dichloromethane (60 mL) under nitrogen for 1 h at rt and then cooled to −40° C. BF$_3$—OEt$_2$ (0.217 mL, 0.29 mmol) was added to the mixture at −40° C. and then warmed to 0° C. The reaction was stirred for 2 h and then quenched with 2 drops of Et$_3$N, diluted with dichloromethane, filtered through Celite and concentrated. Chromatography over silica gel using a gradient of 20-40% EtOAc in Heptane followed by evaporation under reduced pressure provided the crude product as a white solid (2.1 g). Further purification by recrystallization from ethanol gave methyl-3-methoxy-4-{[2S,3R,4S,5R,6R)-3,4,5-tris(acetoxy)-6-[(acetyloxy)methyl]oxan-2-yl]oxy}benzoate (1.4 g, 46%) as a white solid.

Vanillic Acid 4-O-β-D-glucoside (8)

Figure 3:
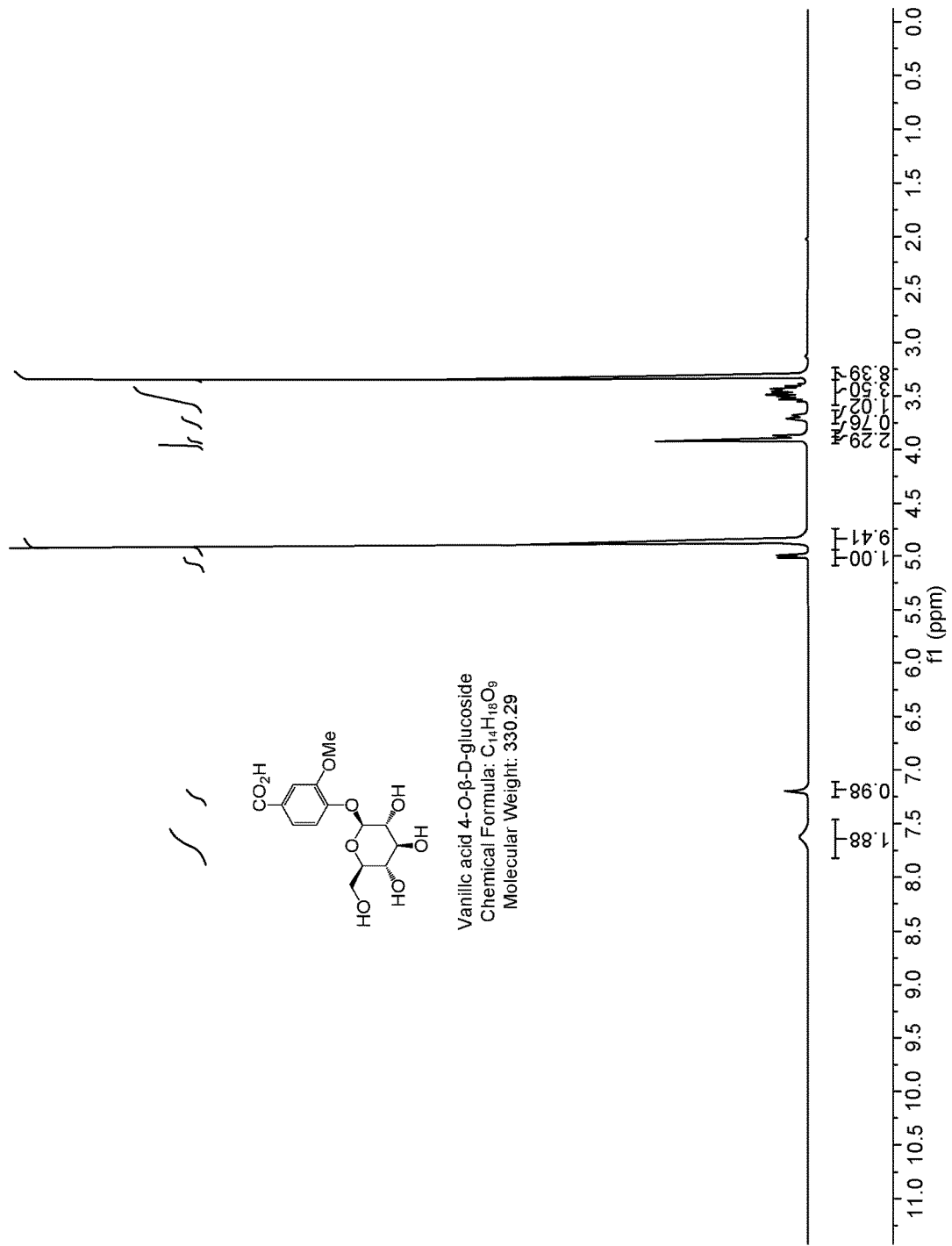

A KOH solution (1.182 g, 21.07 mmol dissolved in 20 mL of water) was added to an ice cooled solution of methyl-3-methoxy-4-{[2S,3R,4S,5R,6R)-3,4,5-tris(acetoxy)-6-[(acetyloxy)methyl]oxan-2-yl]oxy}benzoate (1.2 g, 21.07 mmol) in methanol (20 mL). The mixture was allowed to warm to rt and stir for 16 h. The reaction mixture was then neutralized by treatment with Dowex 50Wx8 ion exchange resin (ca. 7 g). Filtration and removal of volatiles under reduced pressure provided 3-methoxy-4-{[2S,3R,4S,5R,6R)-3,4,5-trihydroxy-6-[(hydroxy)methyl]oxan-2-yl]oxy}benzoic acid as a white solid (0.81 g). Dowex 50Wx8 ion-exchange resin (200-400 mesh) was used as a pre-wash and adjusted to pH=7 to capture the product. The resin was then acidified to pH 3-4 to release product. After evaporation, the crude product was purified by prep HPLC (10% CH$_3$CN in water) and dried by freeze-thaw pump method. LC/MS, 353.2, 348.3. $^1$H NMR of compound (8) is shown in FIG. 3.

Example 1D. Methyl Vanillate 4-O-beta-D-glucoside

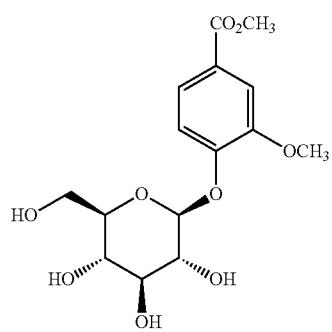

Figure 4:
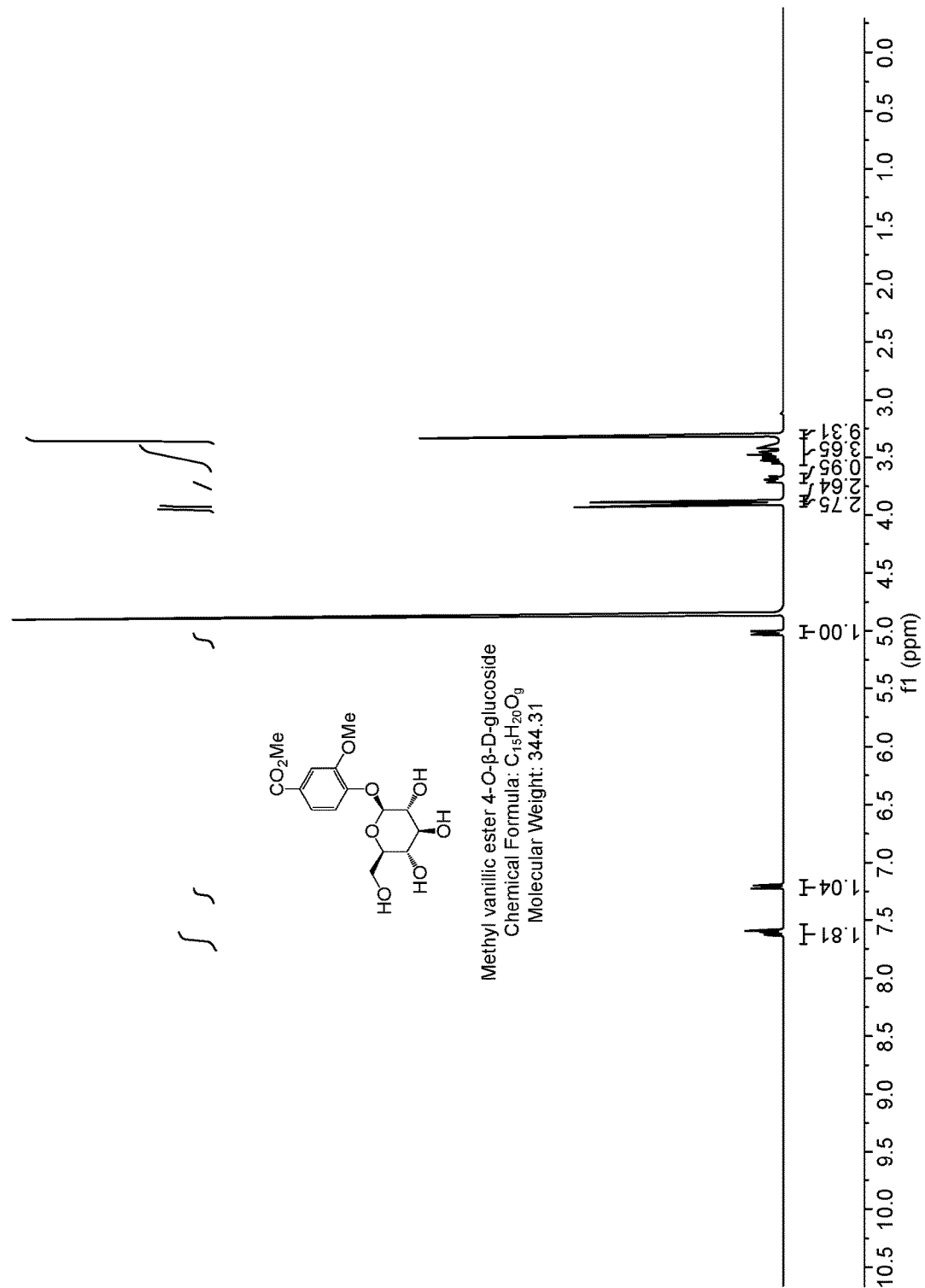

To a solution of methyl-3-methoxy-4-{[2S,3R,4S,5R,6R)-3,4,5-tris(acetoxy)-6-[(acetyloxy)methyl]oxan-2-yl]oxy}benzoate (500 mg, 0.975 mmol) in THF/CH$_3$OH (30 mL, v/v=1:1) was added K$_2$CO$_3$ (13.48 mg, 0.097 mmol). The resulting suspension was stirred at rt for 2 h and then filtered through a pad of Celite. The filtrate was concentrated under reduced pressure to give a white solid, methyl-3-methoxy-{[2S,3R,4S,5R,6R)-3,4,5-trihydroxy-6-[(hydroxy)methyl]oxan-2-yl]oxy}benzoate (360 mg, 107%) which was contaminated with salts. This material was further purified by prep HPLC (10% CH$_3$CN in water) to give the pure product 9 as white solid (300 mg, 89%). LC/MS, 367.0, 362.2. $^1$H NMR of compound (9) is shown in FIG. 4.

Example 1E. Syringic Acid 4-O-beta-D-glucuronide

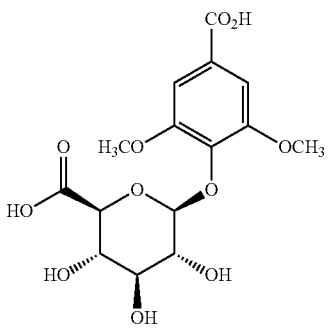

Scheme 3. Synthesis of 2, 3, 4, tri-O-acetyl-I-(2,2,2-trichloroethanimidate)-D-glucopyranuronic acid, methyl ester (13)

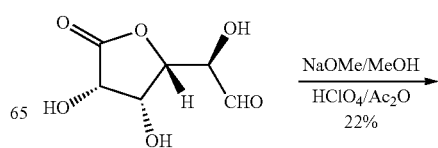

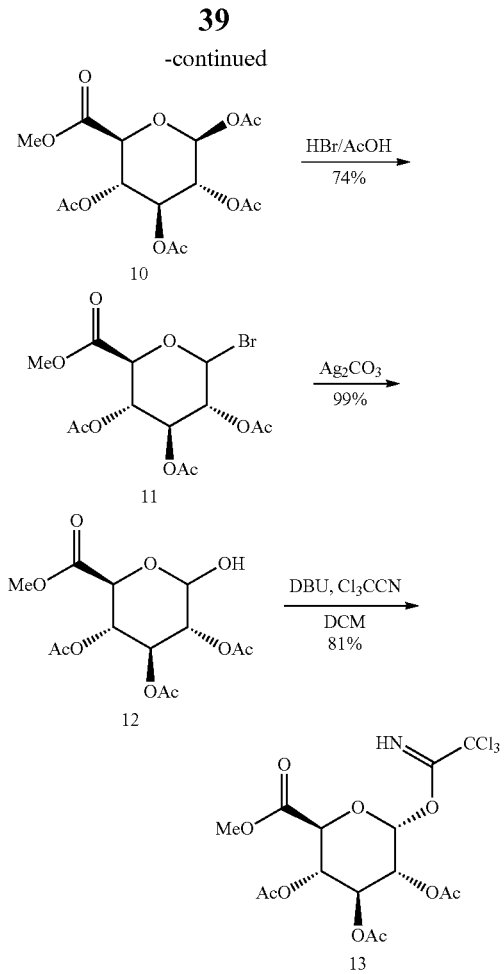

(2S,3R,4S,5S,6S)-6-(methoxycarbonyl)tetrahydro-2H-pyran-2,3,4,5-tetrayl tetraacetate(10)

A mixture of D-(+)-glucuronic acid-gamma-lactone, (2R)-2-[2S,3R,4S)-3,4-dihydroxy-5-oxolan-2-yl]-2-hydroxyacetaldehyde (44 g, 249.8 mmol) and NaOCH$_3$ (0.03 eq, 1.3 mL of 5.4M solution in CH$_3$OH) in CH$_3$OH (250 mL) was stirred for 2 h at rt under nitrogen. The reaction mixture (yellow solution) was concentrated under reduced pressure to yield a yellow-orange oil. The oil was dissolved in acetic anhydride (175 mL) and perchloric acid (0.8 mL) in acetic anhydride (5 mL) was added dropwise to the stirring mixture in an ice bath. The resulting solution was stirred for an additional 2 h. The resulting precipitate was collected by filtration through a sintered glass funnel and washed with water and air dried to yield the tetraacetate as a white solid (21 g, 22%)

(3R,4S,5S,6S)-2-bromo-6-(methoxycarbonyl)tetrahydro-2H-pyran-3,4,5-triyl triacetate (11)

Methyl (2S,3S,4S,5R,6S)-3,4,5,6-tetrakis(acetyloxy)oxane-2-carboxylate (20.6 g. 54.74 mmol) was dissolved in dichloromethane (45 mL) and cooled to 0° C. HBr (33% in acetic acid, 82 mL) was added and the reaction was allowed to warm to rt and stir for 4 h. The reaction mixture was then diluted with ether (250 mL), washed with water (2×70 mL), satd NaHCO$_3$ (500 mL; caution—gas generated), water and brine. The combined organic layers were dried over MgSO$_4$, filtered and concentrated under reduced pressure. The residue was recrystallized using absolute ethanol to give (3R, 4S,5S,6S)-2-bromo-6-(methoxycarbonyl)tetrahydro-2H-pyran-3,4,5-triyl triacetate (11) as a white solid (16.0 g, 74%)

Compound 11 was dissolved in 350 mL of acetone and water (35 mL) and AgCO$_3$ (6.075 g, 22.03 mmol) was added and the reaction mixture stirred for 16 hr. The reaction mixture was filtered through Celite and rinsed with dichloromethane. After removal of solvent under reduced pressure, the residue was dissolved in dichloromethane and washed with water, brine and the organic layer was dried over MgSO$_4$, filtered and solvent was removed under reduced pressure to yield (3R,4S,5S,6S)-2-hydroxy-6-(methoxycarbonyl)tetrahydro-2H-pyran-3,4,5-triyl triacetate (12) as a white solid (14.4 g, 99%)

(2S,3S,4S,5R,6R)-2-methoxycarbonyl-6-(2,2,2-trichloro-1-iminoethoxy)tetrahydro-2H-pyran-3,4,5-triyl triacetate (13)

To compound 12 (14.0 g, 41.88 mmol) in dichloromethane (180 mL) was added trichloroacetonitrile (29.4 mL, 293.2 mmol) followed by 1,8-diazabicyclo[5,4,0] undec-ene (DBU, 0.50 mL) at 0 C under nitrogen. The reaction mixture was stirred for 16 h and then concentrated and purified by silica gel chromatography (30%/0 EtOAc in heptane) to give methyl (2S,3S,4S,5R,6S)-3,4,5-tris(acetoxy)-6-[(trichloroethanimidoyl)oxy]oxane-2-carboxylate (16.3 g, 81%) as an off-white solid.

(2S,3R,4S,5S,6S)-2-(2,6-dimethoxy-4-(methoxycarbonyl)phenoxy)-6-(methoxycarbonyl) tetrahydro-2H-pyran-3,4,5-triyl triacetate (14)

Methyl syringate (739 mg, 3.48 mmol), methyl (2S,3S, 4S,5R,6S)-3,4,5-tris(acetoxy)-6-[(trichloroethanimidoyl)oxy]oxane-2-carboxylate (2.0 g, 4.18 mmol) and 4 A molecular sieves were stirred in anhydrous dichloromethane (35 mL) for 1 h at rt then cooled to −40° C. BF$_3$—OEt$_2$ (0.176 mL, 1.393 mmol) was added to the reaction mixture at −40° C. and the reaction mixture was then warmed to 0° C. After stirring for 2 h, Et$_3$N (2 drops) was added and the reaction mixture was diluted with dichloromethane, filtered and volatiles removed under reduced pressure. Chromatography on silica gel using 20% EtOAc in heptane followed by removed of solvent under reduced pressure yielded methyl (2S,3S,4S,5R,6S)-3,4,5-tris(acetyloxy)-6-[2,6-dimethoxy-4-(methoxycarbonyl)phenoxy]oxane-2-carboxylate as a solid foam which was triturated with ether:heptane (9/1, v/v), filtered and dried in vacuo to give 14 as white solid (1.42 g, 77%).

Syringic Acid 4-O-beta-D-glucuronide (15)

Figure 5:
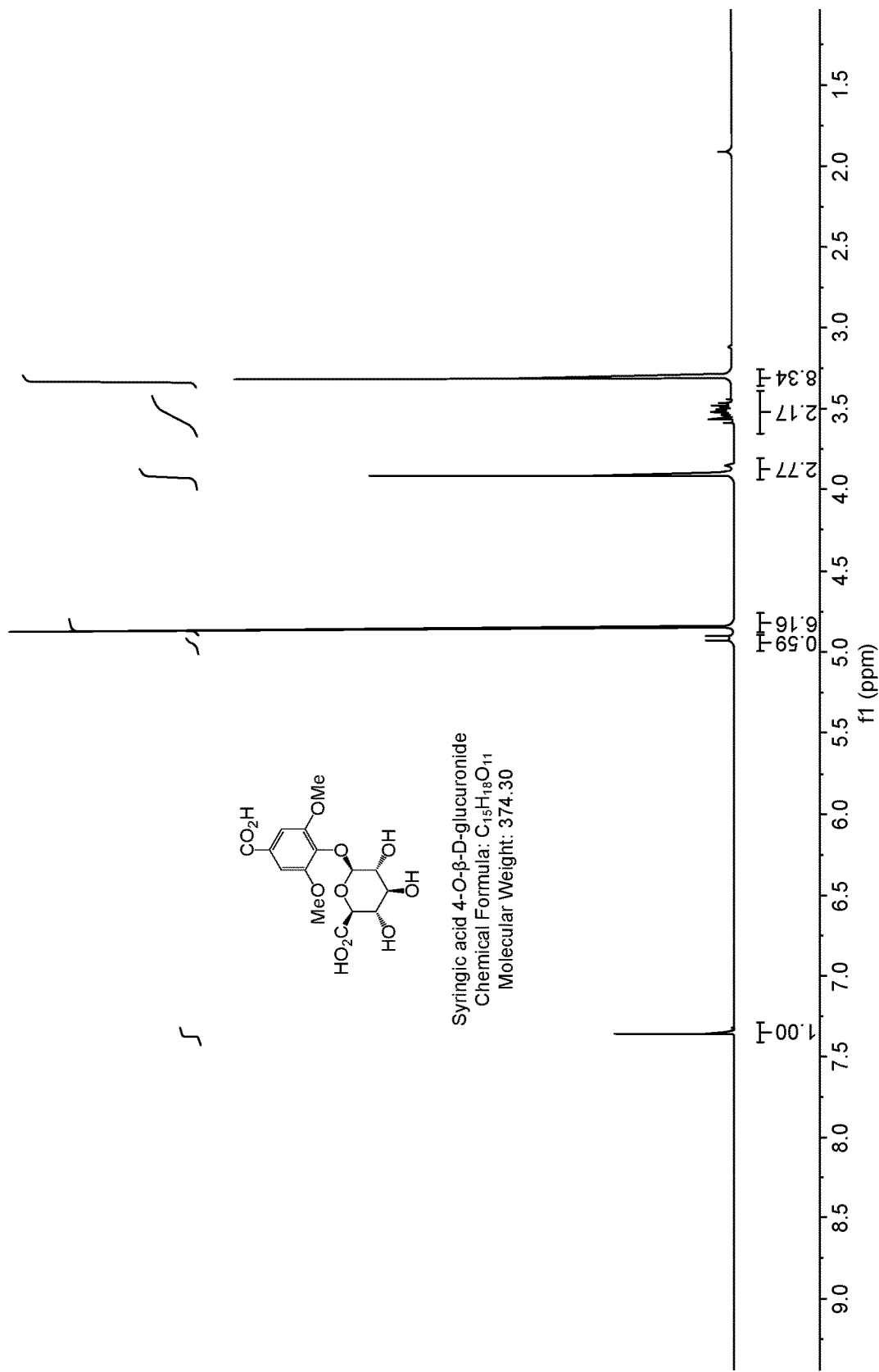

A KOH solution (1.147 g, 20.4 mL dissolved in 24 mL of water) was added to an ice-cooled solution of methyl (2S,3S,4S,5R,6S)-3,4,5-tris(acetyloxy)-6-[2,6-dimethoxy-4-(methoxycarbonyl)phenoxy]oxane-2-carboxylate (1.2 g, 2.27 mmol) in CH$_3$OH (24 mL). The mixture was allowed to warm to t and stirred for 28 hr. The reaction mixture was neutralized by treatment with Dowex 50Wx8 ion-exchange resin (ca. 6 g). After filtration and removal of volatiles under reduced pressure the fully deprotected material was obtained as a white solid which was further purified by prep HPLC (10% CH$_3$OH in water) and removal of volatiles in vacio gave syringic acid 4-O-beta-D-glucuronide (15), as a white solid (0.82 gram, 96%). LC/MS, 397.0, 392.2. $^1$H NMR of compound (15) is shown in FIG. 5.

Example 1F. 3,5-dimethoxy-4-{[(2S,3R,4R,5R,6S)-3,4,5-trihydroxy-6-methyloxan-2-yl]oxy}benzoic acid (28)

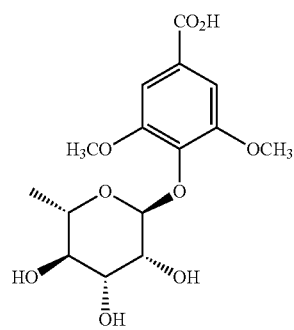

(28)

To a stirred suspension of (2R,3R,4S,5R,6R)-6-methyloxane-2,3,4,5-tetrol hydrate (10 g, 54.90 mmol) in acetic anhydride (39 mL, 411.7 mmol) at 0° C. was added pyridine (40 mL, 494 mmol) over 10 min. The reaction mixture was allowed to warm to rt and stirred for 16 h. The mixture was then concentrated in vacuo, diluted with dichloromethane and washed with 10% HCl (50 mL), satd NaHCO$_3$ and brine. The organic layer was then dried over Na$_2$SO$_4$, filtered and concentrated under reduced pressure to yield (2S,3R,5S,6R)-3,4,5-tris(acetoxy)-6-methyloxan-2-yl acetate as a clear syrup (17.7 g, 97%).

(2S,3R,5S,6R)-3,4,5-tris(acetoxy)-6-methyloxan-2-yl (17.5 g, 52.66 mmol) in THF (60 mL) was treated with acetic acid (3.32 mL, 57.9 mmol) and hydrazine hydrate (2.81 mL, 57.93 mmol) for 4 hrs after which the reaction was extracted once with EtOAc. The combined organic phases were washed with water and dried over MgSO$_4$. Filtration followed by evaporation under reduced pressure gave the crude product as an oil which was recrystallized from hot EtOAc/hexanes to yield the product (2R,3S,4S,5R)-4,5-bis(acetyloxy)-6-hydroxy-2-methyloxan-3-yl acetate as a white solid (9.7 g, 63%).

(2R,3S,4S,5R)-4,5-bis(acetyloxy)-6-hydroxy-2-methyloxan-3-yl acetate (9.5 g, 32.73 mmol) in dichloromethane (50 mL) under nitrogen was cooled to −20° C. and treated with trichloroacetonitrile (16.4 mL, 163.6 mmol) followed by DBU (0.98 mL) over 15 minutes. The reaction was stirred for 2.5 hr and then concentrated in vacuo to give an oil from which the product was isolated by silica gel chromatography (30% EtOAc in heptane) as a clear oil (12.0 g, 84%).

Methyl syringate (2.36 g, 11.12 mmol), (2R,3S,4S,5R)-4,5-bis(acetyloxy)-6-hydroxy-2-methyloxan-3-yl acetate (5.8 g, 13.34 mmol) and 4 Å molecular sieves were stirred in dichloromethane (60 mL) for 1 hr at rt and then cooled to −40° C. BF$_3$—OEt$_2$ (0.563 mL, 4.48 mmol) was added and the reaction mixture was warmed to 0 C and stirred for 2 h. The reaction was quenched with two drops of Et$_3$N, diluted with dichloromethane, filtered and concentrated under reduced pressure. The product, methyl-3,5-dimethoxy-4-{[3R,4S,5S,6R)-3,4,5-tris(acetyloxy)-6-methyloxan-2-yl]oxy}benzoate, was isolated from silica gel chromatography as a foam (3.5 g, 65%)

Figure 7:
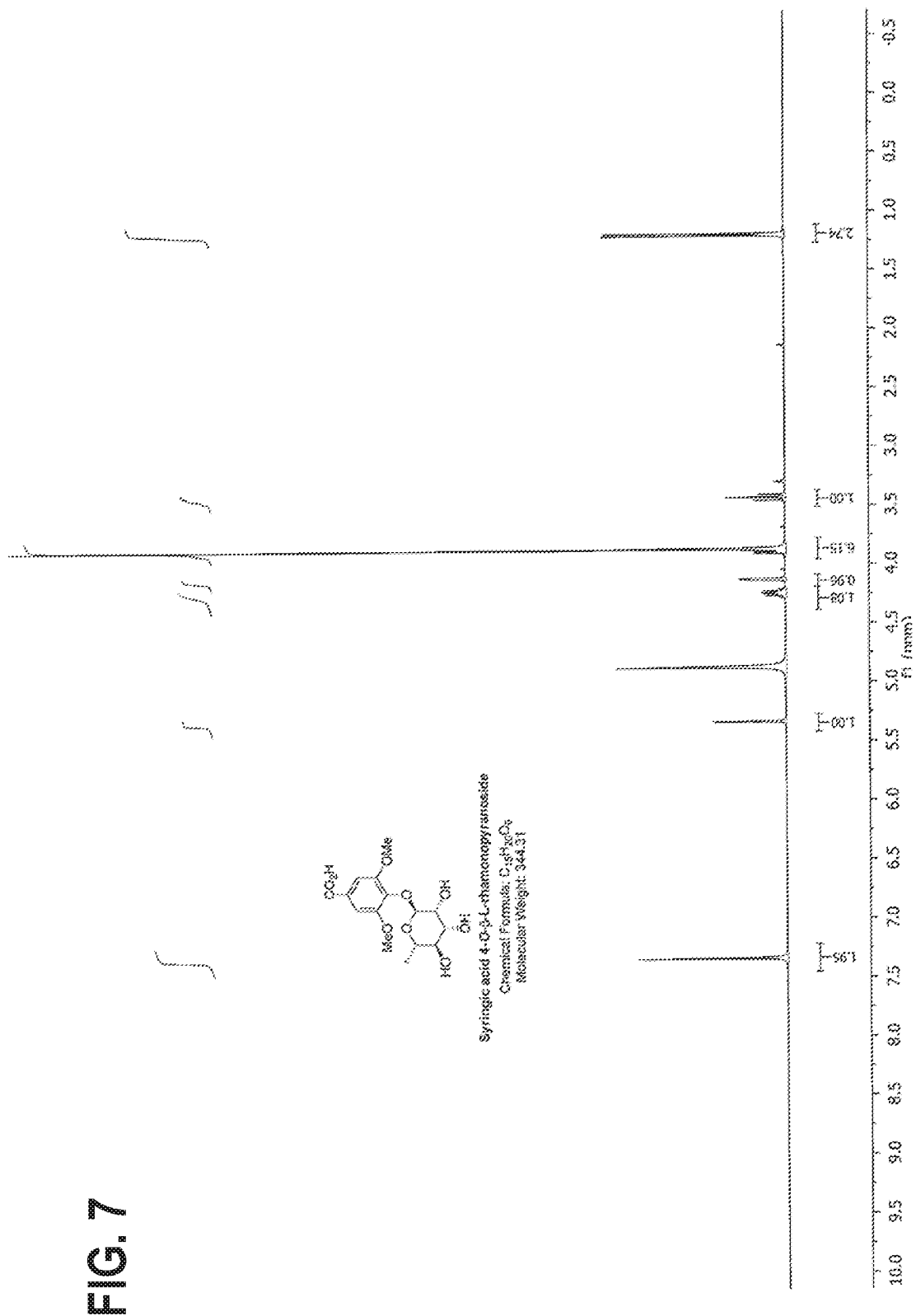

A KOH solution (2.08 g, 37.2 mmol in 40 mL of water) was added to a solution of methyl-3,5-dimethoxy-4-{[3R,4S,5S,6R)-3,4,5-tris(acetyloxy)-6-methyloxan-2-yl]oxy}benzoate in CH$_3$OH at 0° C. The reaction mixture was allowed to warm to rt and stirred for 20 hrs. The reaction mixture was then neutralized with Dowex 50Wx8 ion-exchange resin (ca. 7 g), filtered and concentrated in vacuo to give, 28, 3,5-dimethoxy-4-{[(2S,3R,4R,5R,6S)-3,4,5-trihydroxy-6-methyloxan-2-yl]oxy}benzoic acid as a white solid (1.1 g, 77%). LC/MS, 343.3. $^1$H NMR of compound (28) is shown in FIG. 7.

Example 1G. Syringic Acid 4-O-beta-2-deoxy-D-glucoside

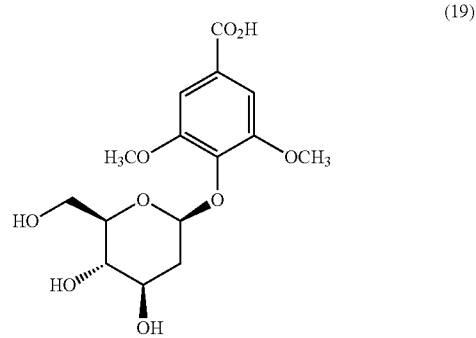 [SMILES: COc1cc(C(=O)O)cc(OC)c1O[C@H]1C[C@@H](O)[C@H](O)[C@@H](CO)O1]

(19)

Synthesis of 2-deoxy-D-glucoside trichloroacetimidates (17) was prepared according to Scheme 5.

Scheme 5. Synthesis of 2-deoxy-D-glucoside trichloroacetimidates (17)

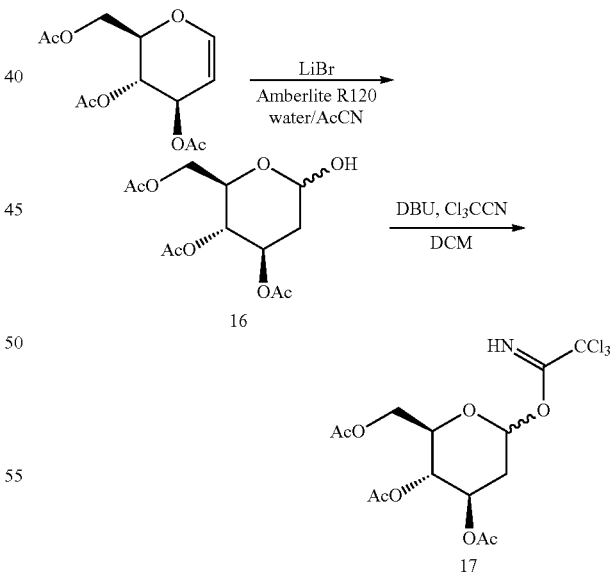

LiBr (59.33 g, 170.8 mmol), AmberliteR120 (58 g, prewashed with CH3CN) and water (48 mL) were added to a solution of tri-O-acetyl-D-glucal (60 g, 55.1 mmol) in CH$_3$CN (1000 mL) at rt. The solvents were then evaporated and the residue suspended between dichloromethane and water. The organic phase was washed with cold 1M HCl solution (200 mL) and with saturated NaHCO$_3$ solution (150 mL) and brine. The organic phase was then dried over MgSO$_4$, filtered and evaporated to dryness under reduced pressure. (2R,3S,4R)-3,4-bis(acetyloxy)-6-hydroxyoxan-2-yl]methyl acetate, 16, was isolated by silica gel chromatography (300/% EtOAc in heptane) as an off-white solid (28.0 g, 44%).

(2R,3S,4R)-3,4-bis(acetyloxy)-6-hydroxyoxan-2-yl]methyl acetate (12.0 g, 41.1 mmol) in dichloromethane (50 mL) was added to trichloroacetonitrile (20.73 mL, 206.7 mmol) followed by DBU (0.62 mL) at 0° C. under nitrogen for 20 hrs. The reaction mixture was then concentrated in vacuo and [(2R,3S,4R)-3,4-bis(acetyloxy)-6-[trichloroethanimidoyl)oxy]oxan-2-yl]methyl acetate, 17, was isolated by silica gel chromatography (30% EtOAc in heptane) as a colorless oil (13.5 g, 75%). Ratio of beta:alpha anomers=10:1.

Methyl syringate (1.83 g, 8.63 mmol), [(2R,3S,4R)-3,4-bis(acetyloxy)-6-[trichloroethanimidoyl)oxy]oxan-2-yl]methyl acetate (4.5 g, 10.35 mmol) and 4 A molecular sieves were stirred in anhydrous dichloromethane (50 mL) for 1 hr at rt and then cooled to −40 C under nitrogen. BF$_3$—OEt$_2$ (0.437 mL, 3.45 mmol) was added dropwise and the reaction mixture was warmed to 0° C. The reaction mixture was then warmed to 0° C. and stirred for 2 hrs after which it was quenched with two drops of Et$_3$N, diluted with dichloromethane, filtered and concentrated. The coupling product methyl 4-{[(4R,5S,6R)-4,5-bis(acetyloxy)-6-[(acetyloxy)methyl]oxan-2-yl]oxy}-3,5-dimethoxybenzoate, 18, was isolated as a light foam solid by silica gel chromatography (20-50% EtOAc in heptane).

Scheme 6. Synthesis of syringic acid 2-deoxy-D-glucosides (19)

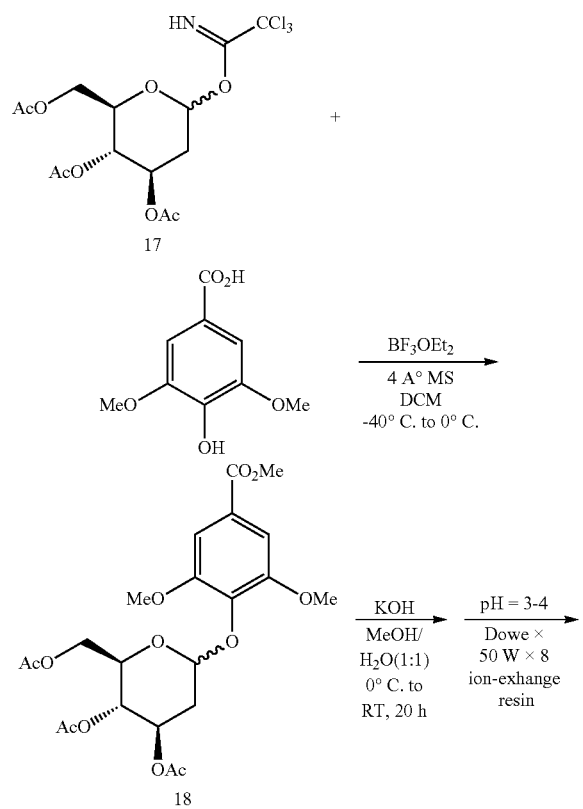

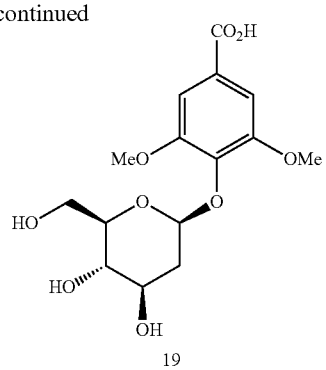

Figure 6:
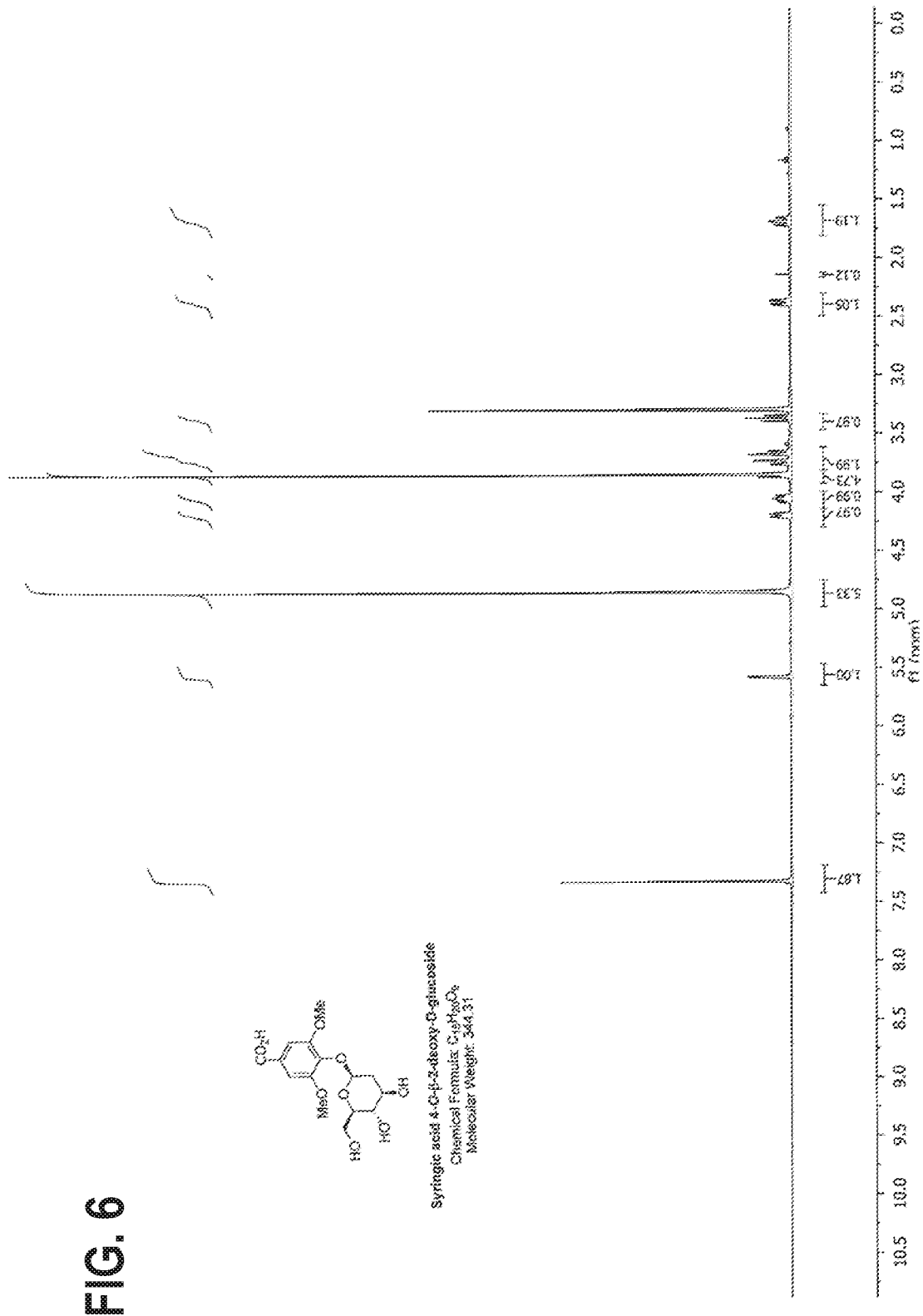

A KOH solution (1.147 g, 20.4 mmol dissolved in 30 mL of water) was added to an ice-cooled solution of methyl methyl 4-{[(4R,5S,6R)-4,5-bis(acetyloxy)-6-[(acetyloxy)methyl]oxan-2-yl]oxy}-3,5-dimethoxybenzoate (1.1 g, 2.27 mmol) in methanol (30 mL). The mixture was allowed to warm to rt and stirred for 16 h. The reaction mixture was then neutralized with Dowex 50Wx8 ion-exchange resin (ca. 5 g). Filtration and removal of volatiles under reduced pressure gave crude product as a white solid. Prep HPLC purification (10% CH$_3$CN in water) gave syringic Acid 4-O-β-2-deoxy-D-glucoside, 19, as a white solid (710 mg, 91%). LC/MS, 365.3, 343.2. $^1$H NMR of compound (19) is shown in FIG. 6.

Example 2. General Procedures for Testing Sweet/Flavor Modifying Ingredients

Sample Preparation Protocol

For testing the material as a sweet/flavor modifying ingredient, two samples were prepared: a 4° Brix high-fructose corn syrup (HFCS) control solution and a 4° Brix HFCS solution with a known concentration of test ingredient.

Sample Preparation

4° Brix HFCS control solution was prepared by adding 50.89 grams of 78.60° Brix HFCS to 1000 g phosphoric acid base which was prepared by adding phosphoric acid dropwise into 1 L of Aquafina Water until pH 3.1 was obtained. pH was measured using a METTLER TOLEDO pH meter.

In the case of a different Brix of HFCS starting syrup, the following formula can be used for the amount of HFCS required to make HFCS control solution.

4° Brix/100*1000 mL/(78.5° Brix/100)=50.96

If any cloudiness persisted, the sample solution was passed through a paper filter. For some low soluble compounds, Branson 2800 Ultra Sonic Bath was used to dissolve the material. If any cloudiness persisted, the sample solution was passed through a paper filter. Solubility was confirmed by shining a laser pointer through the solution. If no diffraction was observed then it was assumed that the material was soluble.

Instructions for Tasters

For each test, 12-16 tasters were presented with these two (2) numbered samples and asked to note the sweet quality differences between the two samples. Tasters were also asked to comment on sweetness onset, sweetness linger, overall sugarlike sweetness and other qualities such as bitter taste, metallic note, astringency, cooling sensation, any offnotes and any associated flavors. Tasters were also asked to assess sample odor differences and provide any descriptions.

Tasters were asked to not to eat at least 1 hour before tasting and rinse with Aquafina water at least 5 times between tasting all samples.

Compound 5 was added at 35 ppm to 4 Brix HFCS in phosphoric acid (as described above). This solution was compared with 4 Brix HFCS in phosphoric acid. A majority of tasters noted a difference and reported qualities such as "rounder sweetness", "more sugar-like" and "earlier onset" for the solution containing compound 5.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed is:

1. A sweetener composition comprising a sweetener and a compound, wherein the compound is selected from the group consisting of

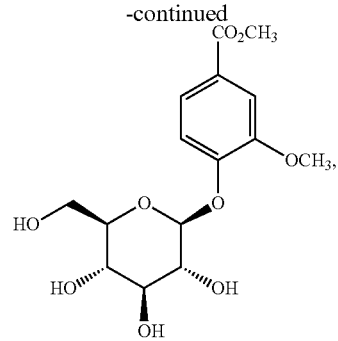

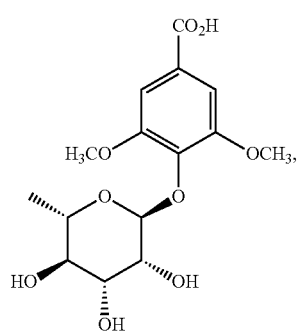

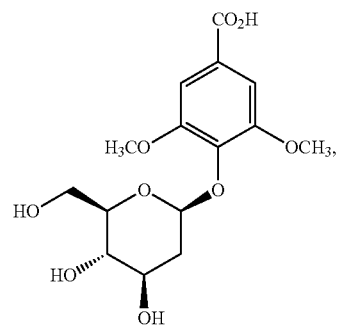

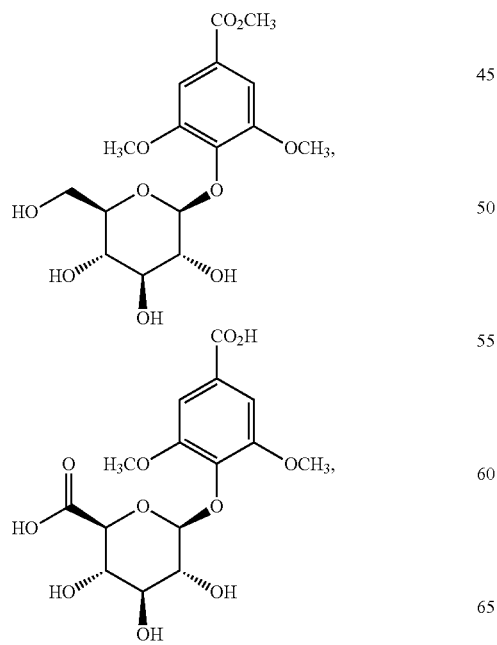

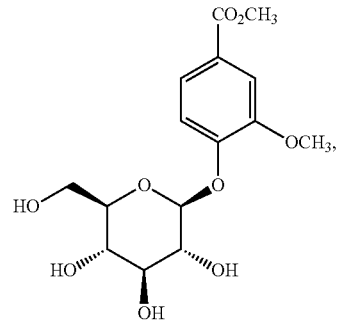

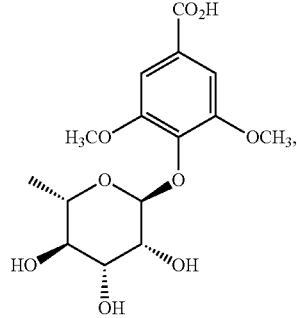 [SMILES: COc1cc(C(=O)O)cc(OC)c1O[C@@H]1O[C@@H](C)[C@H](O)[C@@H](O)[C@H]1O]

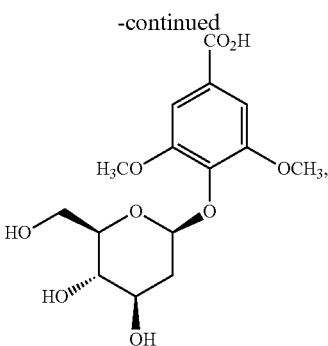

salts thereof, and any combination thereof.

2. The sweetener composition of claim 1, wherein the sweetener is selected from the group consisting of a steviol glycoside, Stevia rebaudiana extracts, Lo Han Guo, Lo Han Guo juice concentrate, Lo Han Guo powder, mogroside V, thaumatin, monellin, brazzein, monatin, erythritol, tagatose, sucrose, liquid sucrose, fructose, liquid fructose, glucose, liquid glucose, high fructose corn syrup, invert sugar, medium invert sugar, maple syrup, maple sugar, honey, chicory syrup, Agave syrup, brown sugar molasses, cane molasses, sugar beet molasses, sorghum syrup, sorbitol, mannitol, maltitol, xylitol, glycyrrhizin, malitol, maltose, lactose, xylose, arabinose, isomalt, lactitol, trehalulose, ribose, fructo-oligosaccharides, aspartame, neotame, alitame, sodium saccharin, calcium saccharin, acesulfame potassium, sodium cyclamate, calcium cyclamate, neohesperidin dihydrochalcone, sucralose, polydextrose, and any mixture thereof.

3. The sweetener composition of claim 1, wherein the sweetener is a non-nutritive sweetener.

4. The sweetener composition of claim 3, wherein the sweetener is a natural non-nutritive sweetener selected from the group consisting of rebaudioside A, rebaudioside B, rebaudioside C, rebaudioside D, rebaudioside M, iso-steviol glycosides, mogrosides, trilobatin, and any combination thereof.

5. The sweetener composition of claim 3, wherein the sweetener is aspartame, acesulfame potassium, steviol glycosides, or any combination thereof.

6. The sweetener composition of claim 1, further comprising a sweetness enhancer.

7. The sweetener composition of claim 6, wherein the sweetness enhancer is selected from the group consisting of D-psicose, erythritol, rubusoside, rebaudioside B, rebaudioside C, trilobatin, phyllodulcin, brazzein, mogrosides, and any combination thereof.

8. The sweetener composition of claim 1, wherein the compound is present in the sweetener composition in a concentration ranging from about 30 ppm to about 300 ppm.

9. A beverage product comprising a sweetener composition of claim 1.

10. A ready-to-drink beverage comprising:
a) water;
b) a sweetener composition of claim 1; and
c) optionally an acidulant selected from the group consisting of phosphoric acid, citric acid, malic acid, tartaric acid, lactic acid, formic acid, ascorbic acid, fumaric acid, gluconic acid, succinic acid, maleic acid, adipic acid, and any mixture thereof.

11. The ready-to-drink beverage of claim 10, wherein the beverage is selected from the group consisting of carbonated beverages, non-carbonated beverages, fountain beverages, frozen carbonated beverages, fruit juices, fruit juice-flavored drinks, fruit-flavored drinks, sports drinks, energy drinks, fortified/enhanced water drinks, soy drinks, vegetable drinks, grain-based drinks, malt beverages, fermented drinks, yogurt drinks, kefir, coffee beverages, tea beverages, dairy beverages, and any mixture thereof.

12. A food product comprising a food component and a sweetener composition of claim 1.

13. A method of modulating sweetness profile of a sweetener in a product, comprising adding to the product a compound selected from the group consisting of

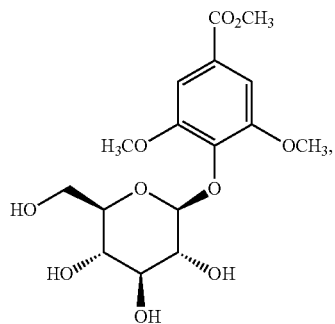

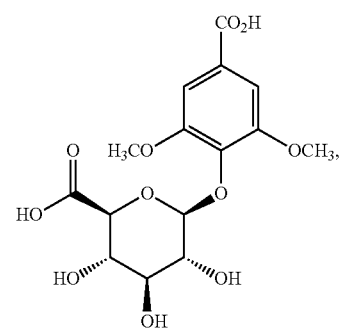

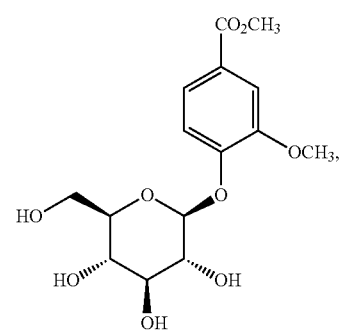

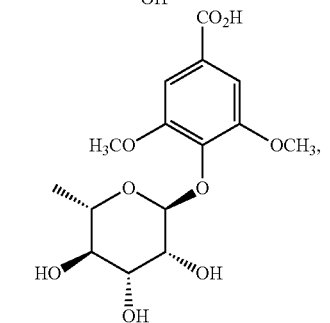

-continued
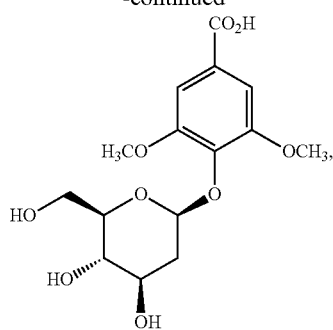
salts thereof, and any combination thereof.
14. A compound having the formula:
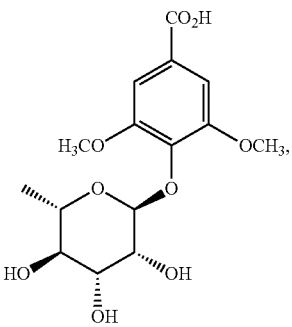
or a salt thereof.
* * * * *